US010946061B2

(12) United States Patent
Glackin

(10) Patent No.: US 10,946,061 B2
(45) Date of Patent: Mar. 16, 2021

(54) PEPTIDE INHIBITORS OF TWIST

(71) Applicant: City of Hope, Duarte, CA (US)

(72) Inventor: Carlotta A. Glackin, Duarte, CA (US)

(73) Assignee: CITY OF HOPE, Duarte, CA (US)

( * ) Notice: Subject to any disclaimer, the term of this patent is extended or adjusted under 35 U.S.C. 154(b) by 0 days.

(21) Appl. No.: 16/843,718

(22) Filed: Apr. 8, 2020

(65) Prior Publication Data

US 2020/0230201 A1 Jul. 23, 2020

Related U.S. Application Data

(62) Division of application No. 15/814,204, filed on Nov. 15, 2017, now Pat. No. 10,646,540.

(60) Provisional application No. 62/424,166, filed on Nov. 18, 2016.

(51) Int. Cl.

| | |
|---|---|
| ***A61K 38/10*** | (2006.01) |
| ***A61K 47/64*** | (2017.01) |
| ***A61K 45/06*** | (2006.01) |
| ***C07K 14/47*** | (2006.01) |
| ***A61K 38/17*** | (2006.01) |
| ***A61K 31/337*** | (2006.01) |
| ***A61K 31/555*** | (2006.01) |
| ***A61K 31/4745*** | (2006.01) |
| ***A61K 33/24*** | (2019.01) |

(52) U.S. Cl.

CPC ............ *A61K 38/10* (2013.01); *A61K 31/337* (2013.01); *A61K 31/4745* (2013.01); *A61K 31/555* (2013.01); *A61K 33/24* (2013.01); *A61K 38/1709* (2013.01); *A61K 45/06* (2013.01); *A61K 47/64* (2017.08); *A61K 47/645* (2017.08); *C07K 14/4702* (2013.01); *C07K 2319/10* (2013.01); *C07K 2319/60* (2013.01); *C07K 2319/70* (2013.01)

(58) Field of Classification Search

None

See application file for complete search history.

(56) References Cited

U.S. PATENT DOCUMENTS

| | | | |
|---|---|---|---|
| 3,773,919 | A | 11/1973 | Boswell et al. |
| 3,991,776 | A | 11/1976 | Duffy |
| 4,076,779 | A | 2/1978 | Skriletz |
| 4,093,709 | A | 6/1978 | Choi et al. |
| 4,118,470 | A | 10/1978 | Casey et al. |
| 4,131,648 | A | 12/1978 | Choi et al. |
| 4,138,344 | A | 2/1979 | Choi et al. |
| 4,293,539 | A | 10/1981 | Ludwig et al. |
| 4,603,044 | A | 7/1986 | Geho et al. |
| 4,675,189 | A | 6/1987 | Kent et al. |
| 4,861,760 | A | 8/1989 | Mazuel et al. |
| 4,911,920 | A | 3/1990 | Jani et al. |
| 5,143,854 | A | 9/1992 | Pirrung et al. |
| 5,212,162 | A | 5/1993 | Missel et al. |
| 5,403,841 | A | 4/1995 | Lang et al. |
| 10,646,540 | B2 | 5/2020 | Glackin |
| 2005/0246794 | A1 | 11/2005 | Khvorova et al. |
| 2007/0298006 | A1 | 12/2007 | Tomalia et al. |
| 2008/0267903 | A1 | 10/2008 | Uchegbu et al. |
| 2010/0255023 | A1 | 10/2010 | Chen |
| 2010/0286237 | A1 | 11/2010 | Birrer et al. |
| 2011/0189694 | A1 * | 8/2011 | Woloszczuk ....... G01N 33/6887 435/7.1 |
| 2011/0224286 | A1 | 9/2011 | Yu et al. |
| 2011/0263675 | A1 | 10/2011 | Federov et al. |
| 2012/0053079 | A1 | 3/2012 | Samant et al. |
| 2012/0207795 | A1 | 8/2012 | Zink et al. |
| 2014/0024610 | A1 | 1/2014 | Pisani et al. |
| 2014/0294752 | A1 | 10/2014 | Kim et al. |
| 2016/0044913 | A1 | 2/2016 | Deikman et al. |
| 2016/0354474 | A1 | 12/2016 | Cohen et al. |
| 2017/0143641 | A1 | 5/2017 | Peer |
| 2017/0173169 | A1 | 6/2017 | Yantasee et al. |
| 2017/0233733 | A1 | 8/2017 | Glackin et al. |
| 2018/0028458 | A1 | 2/2018 | Buschmann et al. |

FOREIGN PATENT DOCUMENTS

| | | | |
|---|---|---|---|
| WO | WO-96/17958 | A1 | 6/1996 |
| WO | WO-2015/089419 | A2 | 6/2015 |
| WO | WO-2015/089419 | A3 | 6/2015 |
| WO | WO-2015/089419 | A9 | 6/2015 |

OTHER PUBLICATIONS

Al-Muhammed, J. et al. (May-Jun. 1996). "In-vivo studies on dexamethasone sodium phosphate liposomes," J Microencapsul 13(3):293-306.

Bastid, J. et al. (2010). "Role of TWIST proteins in cancer progression," *Atlas Genet Cytogenet Oncol Haematol.* 14(9):898-844.

Bettinger, T. et al. (Apr. 2001). "Recent developments in RNA-based strategies for cancer gene therapy," *Curr Opin Mol Ther* 3(2):116-124.

Blackman, M.L. et al. (Oct. 15, 2008, e-published Sep. 18, 2008). "Tetrazine ligation: fast bioconjugation based on inverse-electron-demand Diels-Alder reactivity," J Am Chem Soc 130(41):13518-13519.

Bohacek, R.S. et al. (Jan. 1996). "The art and practice of structure-based drug design: a molecular modeling perspective," *Med Res Rev* 16(1):3-50.

Bramsen, J.B. et al. (Aug. 20, 2012). "Development of Therapeutic-Grade Small Interfering RNAs by Chemical Engineering," *Frontiers in Genetics* 3:154, 7 pages.

(Continued)

*Primary Examiner* — Jeanette M Lieb

(74) *Attorney, Agent, or Firm* — Mintz, Levin, Cohn, Ferris, Glovsky and Popeo, P.C.

(57) ABSTRACT

The disclosure provides, inter alia, compositions comprising TWIST peptide inhibitors and optionally one or more anti-cancer agents, and methods of using the compositions for the treatment of cancer.

20 Claims, 7 Drawing Sheets

Specification includes a Sequence Listing.

(56) References Cited

OTHER PUBLICATIONS

Bridges, R.S .et al. (Dec. 2009, e-published Nov. 5, 2009). "Gene expression profiling of pulmonary fibrosis identifies Twist1 as an antiapoptotic molecular "rectifier" of growth factor signaling," *Am J Pathol* 165(6):2351-2361.
Chang, A.T. et al. (Mar. 15, 2015, e-published Mar. 11, 2015). "An evolutionarily conserved DNA architecture determines target specificity of the TWIST family bHLH transcription factors," *Genes Dev* 29(6):603-616.
Chen, Y.Q. et al. (Jan. 1998). "A novel DNA recognition mode by the NF-kappa B p65 homodimer," Nat Struct Biol 5(1):67-73.
Chonn, A. et al. (Dec. 1995). "Recent advances in liposomal drug-delivery systems," *Curr Opin Biotechnol* 6(6):698-708.
Coelho, T. et al. (Aug. 29, 2013). "Safety and efficacy of RNAi therapy for transthyretin amyloidosis," N Engl J Med 369(9):819-829.
Database Accession No. NM_001271893.3 (Sep. 24, 2018), 4 pages.
Database Accession No. NM_000474.3 (Nov. 10, 2018). 4 pages.
Database Accession No. NP_001258822.1 (May 1, 2019). 3 pages.
Database Accession No. NP_00465.1 (May 7, 2019). 3 pages.
Devaraj, n. K. et al. (Dec. 2008). "Tetrazine-based cycloadditions: application to pretargeted live cell imaging," *Bioconjug Chem* 19(12):2297-2299.
Elghouzzi, V. et al. (Mar. 22, 2000). "Saethre-Chotzen mutations cause TWIST protein degradation or impaired nuclear location," Hum Mol Genet 9(5):813-819.
Evans, R.A. (2007). "The Rise of Azide-Alkyne 1,3-Dipolar 'Click' Cycloaddition and its Application to Polymer Science and Surface Modification," Australian Journal of Chemistry 60(6):384-395.
Eyles, J.E. et al. (Jul. 1997). "Oral delivery and fate of poly(lactic acid) microsphere-encapsulated interferon in rats," J. Pharm. Pharmacol. 49(7):669-674.
Feng, M.Y. et al. (2009, e-published Oct. 6, 2009). "Metastasis-induction and apoptosis-protection by TWIST in gastric cancer cells," *Clin Exp Metastasis* 26(8):1013-1023.
Ferlay, J. et al. (Mar. 2010, e-published Jan. 29, 2010). "Estimates of cancer incidence and mortality in Europe in 2008," Eur J Cancer 46(4):765-781.
Finlay, J. et al. (2015, e-published Feb. 11, 2015). "RNA-based TWIST1 inhibition via dendrimer complex to reduce breast cancer cell metastasis," *Biomed Res Int* 2015:382745.
Finlay, J. et al. (Oct. 2015, e-published Jun. 24, 2015). "Mesoporous silica nanoparticle delivery of chemically modified siRNA against TWIST1 leads to reduced tumor burden," *Nanomedicine* 11(7):1657-1666.
Fodor, S.P. et al. (Feb. 15, 1991). "Light-directed, spatially addressable parallel chemical synthesis," *Science* 251(4995):767-773.
Fu, J. et al. (Feb. 2011, e-published Aug. 17, 2010). "The TWIST/Mi2/NuRD protein complex and its essential role in cancer metastasis," Cell Res 21(2):275-289.
Gajula, R.P. et al. (Nov. 2013, e-published Aug. 27, 2013). "The twist box domain is required for Twist1-induced prostate cancer metastasis," *Mol Cancer Res* 11(11):1387-1400.
Gao, Z.H. et al. (Jun. 1995). "Controlled release of a contraceptive steroid from biodegradable and injectable gel formulations: in vitro evaluation," Pharm. Res 12(6):857-863.
Haslehurst, A.M. et al. (Mar. 19, 2012). "EMT transcription factors snail and slug directly contribute to cisplatin resistance in ovarian cancer," BMC Cancer12:91.
Herce, H.D. et al. (Oct. 7, 2009). "Arginine-rich peptides destabilize the plasma membrane, consistent with a pore formation translocation mechanism of cell-penetrating peptides," *Biophys J* 97(7):1917-1925.
Hoyle, C.E. et al. (Feb. 22, 2010). "Thiol-ene click chemistry," Angew Chem Int Ed Engl 49(9):1540-1573.
Johnston, M. (Feb. 26, 1998). "Gene chips: array of hope for understanding gene regulation," *Curr Biol* 8(5):R171-174.
Journal of Polymer Science: Polymer Letters Edition (1980). "Preparation of Polyacetals by the Relaxation of Divinyl Ethers and Polyols," 18:293-297.
Kern, S. et al. (Jul. 1997). "Direct hybridization of large-insert genomic clones on high-density gridded cDNA filter arrays," Biotechniques 23(1):120-124.
Kolb, H.C. et al (Jun. 1, 2001). "Click Chemistry: Diverse Chemical Function from a Few Good Reactions," *Angewandte Chemie International Edition* 40(11):2004-2021.
Kong, D. et al. (Feb. 21, 2011). "Cancer Stem Cells and Epithelial-to-Mesenchymal Transition (EMT)-Phenotypic Cells: Are They Cousins or Twins?" Cancers 3(1):716-729.
Li, Y. et al. (Jan. 2011). "Prophylactic, therapeutic and immune enhancement effect of liposome-encapsulated PolyICLC on highly pathogenic H5N1 influenza infection," *J Gene Med* 13(1):60-72.
Li, S et al. (Aug. 14, 2012). "TWIST1 associates with NF-κB subunit RELA via carboxyl-terminal WR domain to promote cell autonomous invasion through IL8 production," *BMC Biol* 10:73.
Li, C. et al. (Nov. 2012, e-published Apr. 11, 2012). "Twist overexpression promoted epithelial-to-mesenchymal transition of human peritoneal mesothelial cells under high glucose," *Nephrol Dial Treatment* 27(11):4119-4124.
Little, S.R. et al. (Jun. 29, 2004, e-published Jun. 21, 2004). "Poly-β amino ester-containing microparticles enhance the activity of nonviral genetic vaccines," PNAS USA 101(26):9534-9539.
Low-Marcheli, J.M. et al. (Jan. 15, 2013). "Twist1 induces CCL2 and recruits macrophages to promote angiogenesis," *Cancer Res* 73(2):662-671.
Lu, D. et al. (Dec. 1994). "Optimization of methods to achieve mRNA-mediated transfection of tumor cells in vitro and in vivo employing cationic liposome vectors," *Cancer Gene Ther* 1(4):245-252.
McNamara. M.A. et al. (2015, e-published Nov. 19, 2015). "RNA-Based Vaccines in Cancer Immunotherapy," *J Immunol Res* 2015:794528, 9 pages.
Meng, H. et al. (Aug. 24, 2010). "Engineered design of mesoporous silica nanoparticles to deliver doxorubicin and P-glycoprotein siRNA to overcome drug resistance in a cancer cell line," *ACS Nano* 4(8):4539-4550.
Murray, S.S. et al. (Oct. 1992). "Expression of helix-loop-helix regulatory genes during differentiation of mouse osteoblastic cells," J Bone Miner Res 7(10):1131-1138.
Nguyen, D.X. et al. (Apr. 2009). "Metastasis: from dissemination to organ-specific colonization," *Nat Rev Cancer* 9(4):274-284.
Ostro, M.J. et al. (Aug. 1989). "Use of liposomes as injectable-drug delivery systems," *Am J Hosp Pharm* 46(8):1576-1587.
Pham, D. et al. (Jul. 15, 2012, e-published Jun. 8, 2012). "Twist1 regulates Ifng expression in Th1 cells by interfering with Runx3 function," *J Immunol* 189(2):832-840.
Phua, K.K. et al. (Mar. 28, 2013, e-published Jan. 7, 2013). "Transfection efficiency and transgene expression kinetics of mRNA delivered in naked and nanoparticle format," *J Control Release* 166(3):227-233.
Phua, K.K. et al. (Jun. 4, 2014). "Intranasal mRNA nanoparticle vaccination induces prophylactic and therapeutic anti-tumor immunity," *Sci Rep* 4:5128.
Phua, K.K. et al. (Jul. 21, 2014). "Messenger RNA (mRNA) nanoparticle tumour vaccination," *Nanoscale* 6(14):7715-7729.
Piccinin, S. et al. (Sep. 11, 2012). "A "twist box" code of p53 inactivation: twist box: p53 interaction promotes p53 degradation," *Cancer Cell* 22(3):404-415.
Pichon, C. et al. (2013). "Mannosylated and histidylated LPR technology for vaccination with tumor antigen mRNA," Methods Mol Biol 969:247-274.
Rahme, G.J. et al. (Jan. 2, 2015, e-published Jan. 13, 2014). "Id4 suppresses MMP2-mediated invasion of glioblastoma-derived cells by direct inactivation of Twist1 function," *Oncogene* 34(1):53-62.
Rao. K.P. (1995). "Recent developments of collagen-based materials for medical applications and drug delivery systems" *J. Biomater Sci. Polym. Ed.* 7(7):623-645.
Sayour, E.J. et al. (2015). "Bridging infection disease vaccines with cancer immunotherapy: a role for targeted RNA based immunotherapeutics," *Journal for Immunotherapy of Cancer* 3:13.

(56) References Cited

OTHER PUBLICATIONS

Schummer, M. et al. (Dec. 1997). "Inexpensive handheld device for the construction of high-density nucleic acid arrays," *Biotechniques* 23(6):1087-1092.
Schwendener, R.A. et al. (Nov. 2014). "Liposomes as vaccine delivery systems: a review of the recent advances," *Ther Adv Vaccines* 2(6):159-182.
Simpson, P. et al. (Nov. 1983). "Maternal-Zygotic Gene Interactions during Formation of the Dorsoventral Pattern in *Drosophila* Embryos," Genetics 105(3):615-632.
Spiteri, C. et al. (2010). "Copper-catalyzed azide-alkyne cycloaddition: regioselective synthesis of 1,4,5-trisubstituted 1,2,3-triazoles," *Angew Chem Int Ed Engl* 49(1):31-33.
Stöckmann, H. et al. (Nov. 7, 2011, e-published Sep. 13, 2011). "Exploring isonitrile-based click chemistry for ligation with biomolecules," *Org Biomol Chem* 9(21):7303-7305.
Su, X. et al. (2011). "In Vitro and in Vivo mRNA Delivery Using Lipid-Enveloped pH-Responsive Polymer Nanoparticles," Molecular Pharmaceutics 8(3):774-787.
Tabernero, J. et al. (Apr. 2013, e-published Jan. 28, 2013). "First-in-humans trial of an RNA interference therapeutic targeting VEGF and KSP in cancer patients with liver involvement," *Cancer Discov* 3(4):406-417.
Teng, Y. et al. (Mar. 2014, e-published Oct. 26, 2013). "The roles of HLH transcription factors in epithelial mesenchymal transition and multiple molecular mechanisms," *Clin Exp Metastasis* 31(3):367-377.
Trimble, E.L et al. (Aug. 2001). "Treatment of platinum-resistant ovarian cancer," Expert Opin Pharmacother 2(8):1299-1306.
Vanjaarsveld, M.T. et al. (Sep. 5, 2013, e-published Oct. 8, 2012). "miR-141 regulates KEAP1 and modulates cisplatin sensitivity in ovarian cancer cells," Oncogene 32(36):4284-4293.
Vernon, A.E. et al. (Sep. 7, 2004). "Tumor metastasis: a new twist on epithelial-mesenchymal transitions," *Curr Biol* 14(17):R719-721.
Vesuna, F. et al. (Dec. 2009). "Twist modulates breast cancer stem cells by transcriptional regulation of CD24 expression," *Neoplasia* 11(12):1318-1328.
Vincentz, J.W. et al. (Mar. 2013, e-published Mar. 21, 2013). "Twist1 controls a cell-specification switch governing cell fate decisions within the cardiac neural crest," *PLoS Genet* 9(3):e1003405.
Wang, S.M .et al. (Mar. 10 1997). "Cloning of the human twist gene: its expression is retained in adult mesodermally-derived tissues," *Gene* 187(1):83-92.
Wang, Y. et al. (Nov. 2011, e-published Jul. 13, 2011). "Autocrine production of interleukin-8 confers cisplatin and paclitaxel resistance in ovarian cancer cells," *Cytokine* 56(2)365-375.
Wasungu, L. et al. (Nov. 28, 2006, e-published Jun. 28, 2006). "Cationic lipids, lipoplexes and intracellular delivery of genes," J Control Release 116(2):255-264.
Yang, J. et al. (Jun. 25, 2004). "Twist, a master regulator of morphogenesis, plays an essential role in tumor metastasis," *Cell* 117(7):927-939.
Yang, J. et al. (Apr. 2015, e-published Feb. 3, 2015). "Overexpression of inhibitor of DNA-binding 2 attenuates pulmonary fibrosis through regulation of c-Abl and Twist," *Am J Pathol* 185(4):1001-1011.
Zhang, J. et al. (Apr. 2012, e-published Dec. 8, 2011). "Aberrant expression of the transcriptional factor Twist1 promotes invasiveness in ALK-positive anaplastic large cell lymphoma," *Cell Signal* 24(4):852-858.
Zuris, J.A. et al. (Jan. 2015, e-published Oct. 30, 2014). "Cationic lipid-mediated delivery of proteins enables efficient protein-based genome editing in vitro and in vivo." *Nat Biotechnol* 33(1):73-80.

* cited by examiner

FIG. 1A
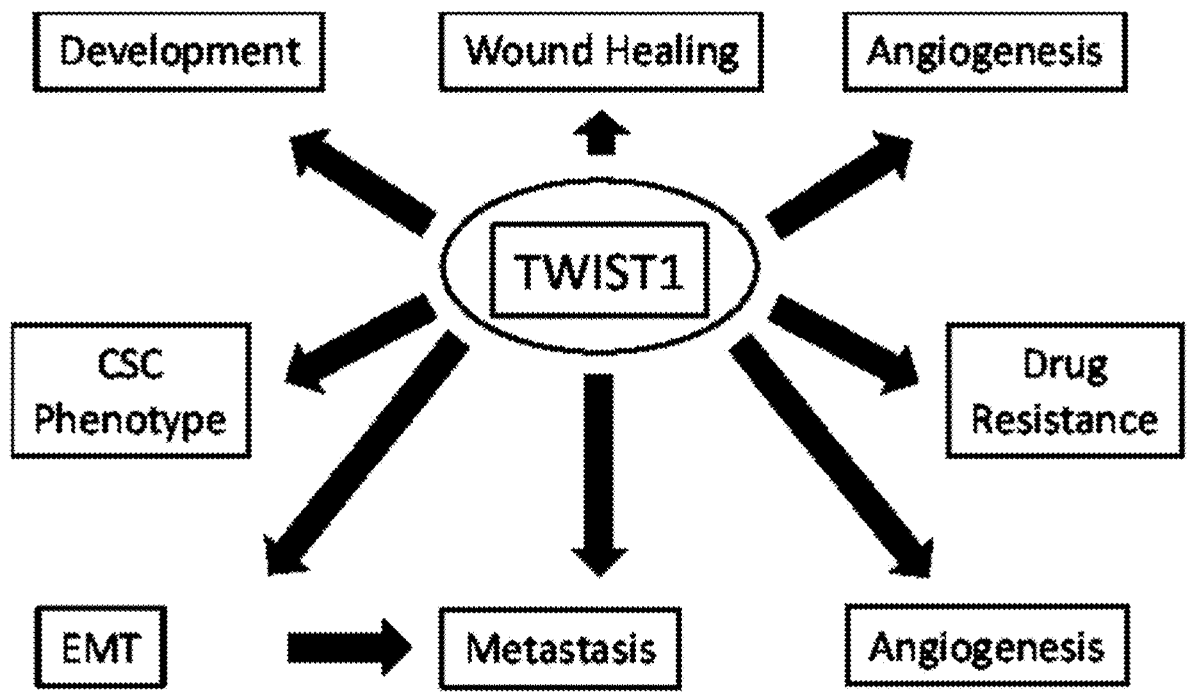
FIG. 1B
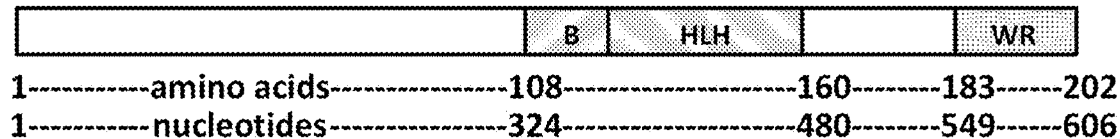
FIG. 1C
190 191 193
| | | | |
|---|---|---|---|
| H. sapiens | 183 | LSYAFSVWRMEGAWSMSASH | 202 |
| M. musculus | 187 | LSYAFSVWRMEGAWSMSASH | 206 |
| X. laevis | 147 | LSYAFSVWRMEGAWSMSASH | 166 |
| D. rerio | 152 | LSYAFSVWRMEGAWSMSTSH | 171 |
| D. melanogaster | 472 | LSYLFGVWRMEGDAQHQKA- | 490 |

SEQUENCE LISTING

```
<160> NUMBER OF SEQ ID NOS: 23

<210> SEQ ID NO 1
<211> LENGTH: 20
<212> TYPE: PRT
<213> ORGANISM: Artificial sequence
<220> FEATURE:
<223> OTHER INFORMATION: Synthetic Polypeptide

<400> SEQUENCE: 1

Leu Ser Tyr Ala Phe Ser Val Trp Arg Met Glu Gly Ala Trp Ser Met
1               5                   10                  15

Ser Ala Ser His
            20


<210> SEQ ID NO 2
<211> LENGTH: 20
<212> TYPE: PRT
<213> ORGANISM: Artificial sequence
<220> FEATURE:
<223> OTHER INFORMATION: Synthetic Polypeptide

<400> SEQUENCE: 2

Leu Ser Tyr Ala Phe Ser Val Trp Arg Met Glu Gly Ala Trp Ser Met
1               5                   10                  15

Ser Thr Ser His
            20


<210> SEQ ID NO 3
<211> LENGTH: 19
<212> TYPE: PRT
<213> ORGANISM: Artificial sequence
<220> FEATURE:
<223> OTHER INFORMATION: Synthetic Polypeptide

<400> SEQUENCE: 3
```

-continued

```
Leu Ser Tyr Leu Phe Gly Val Trp Arg Met Glu Gly Asp Ala Gln His
1               5                   10                  15

Gln Lys Ala


<210> SEQ ID NO 4
<211> LENGTH: 9
<212> TYPE: PRT
<213> ORGANISM: Artificial sequence
<220> FEATURE:
<223> OTHER INFORMATION: Synthetic Polypeptide

<400> SEQUENCE: 4

Arg Arg Arg Arg Arg Arg Arg Arg Arg
1               5


<210> SEQ ID NO 5
<211> LENGTH: 7
<212> TYPE: PRT
<213> ORGANISM: Artificial sequence
<220> FEATURE:
<223> OTHER INFORMATION: Synthetic Polypeptide

<400> SEQUENCE: 5

Arg Arg Arg Arg Arg Arg Arg
1               5


<210> SEQ ID NO 6
<211> LENGTH: 13
<212> TYPE: PRT
<213> ORGANISM: Artificial sequence
<220> FEATURE:
<223> OTHER INFORMATION: Synthetic Polypeptide

<400> SEQUENCE: 6

Gly Arg Lys Lys Arg Arg Gln Arg Arg Arg Pro Pro Gln
1               5                   10


<210> SEQ ID NO 7
<211> LENGTH: 16
<212> TYPE: PRT
<213> ORGANISM: Artificial sequence
<220> FEATURE:
<223> OTHER INFORMATION: Synthetic Polypeptide

<400> SEQUENCE: 7

Arg Gln Ile Lys Ile Trp Phe Gln Asn Arg Arg Met Lys Trp Lys Lys
1               5                   10                  15


<210> SEQ ID NO 8
<211> LENGTH: 15
<212> TYPE: PRT
<213> ORGANISM: Artificial sequence
<220> FEATURE:
<223> OTHER INFORMATION: Synthetic Polypeptide

<400> SEQUENCE: 8

Arg Arg Arg Arg Asn Arg Thr Arg Arg Asn Arg Arg Arg Val Arg
1               5                   10                  15


<210> SEQ ID NO 9
<211> LENGTH: 18
<212> TYPE: PRT
<213> ORGANISM: Artificial sequence
<220> FEATURE:
<223> OTHER INFORMATION: Synthetic Polypeptide
```

<400> SEQUENCE: 9

Leu Leu Ile Ile Leu Arg Arg Arg Ile Arg Lys Gln Ala His Ala His
1 5 10 15

Ser Lys

<210> SEQ ID NO 10
<211> LENGTH: 27
<212> TYPE: PRT
<213> ORGANISM: Artificial sequence
<220> FEATURE:
<223> OTHER INFORMATION: Synthetic Polypeptide

<400> SEQUENCE: 10

Gly Trp Thr Leu Asn Ser Ala Gly Tyr Leu Leu Gly Lys Ile Asn Leu
1 5 10 15

Lys Ala Leu Ala Ala Leu Ala Lys Lys Ile Leu
20 25

<210> SEQ ID NO 11
<211> LENGTH: 22
<212> TYPE: PRT
<213> ORGANISM: Artificial sequence
<220> FEATURE:
<223> OTHER INFORMATION: Synthetic Polypeptide

<400> SEQUENCE: 11

Met Val Thr Val Leu Phe Arg Arg Leu Arg Ile Arg Arg Ala Cys Gly
1 5 10 15

Pro Pro Arg Val Arg Val
20

<210> SEQ ID NO 12
<211> LENGTH: 202
<212> TYPE: PRT
<213> ORGANISM: Artificial sequence
<220> FEATURE:
<223> OTHER INFORMATION: Synthetic Polypeptide

<400> SEQUENCE: 12

Met Met Gln Asp Val Ser Ser Ser Pro Val Ser Pro Ala Asp Asp Ser
1 5 10 15

Leu Ser Asn Ser Glu Glu Glu Pro Asp Arg Gln Gln Pro Pro Ser Gly
20 25 30

Lys Arg Gly Gly Arg Lys Arg Arg Ser Ser Arg Arg Ser Ala Gly Gly
35 40 45

Gly Ala Gly Pro Gly Gly Ala Ala Gly Gly Gly Val Gly Gly Gly Asp
50 55 60

Glu Pro Gly Ser Pro Ala Gln Gly Lys Arg Gly Lys Lys Ser Ala Gly
65 70 75 80

Cys Gly Gly Gly Gly Gly Ala Gly Gly Gly Gly Gly Ser Ser Ser Gly
85 90 95

Gly Gly Ser Pro Gln Ser Tyr Glu Glu Leu Gln Thr Gln Arg Val Met
100 105 110

Ala Asn Val Arg Glu Arg Gln Arg Thr Gln Ser Leu Asn Glu Ala Phe
115 120 125

Ala Ala Leu Arg Lys Ile Ile Pro Thr Leu Pro Ser Asp Lys Leu Ser
130 135 140

Lys Ile Gln Thr Leu Lys Leu Ala Ala Arg Tyr Ile Asp Phe Leu Tyr
145 150 155 160

```
Gln Val Leu Gln Ser Asp Glu Leu Asp Ser Lys Met Ala Ser Cys Ser
                165                 170                 175

Tyr Val Ala His Glu Arg Leu Ser Tyr Ala Phe Ser Val Trp Arg Met
            180                 185                 190

Glu Gly Ala Trp Ser Met Ser Ala Ser His
        195                 200


<210> SEQ ID NO 13
<211> LENGTH: 1669
<212> TYPE: DNA
<213> ORGANISM: Artificial sequence
<220> FEATURE:
<223> OTHER INFORMATION: Synthetic Polynucleotide

<400> SEQUENCE: 13

gaggtataag agcctccaag tctgcagctc tcgcccaact cccagacacc tcgcgggctc     60

tgcagcaccg gcaccgtttc caggaggcct ggcggggtgt gcgtccagcc gttgggcgct    120

ttctttttgg acctcggggc catccacacc gtcccctccc cctcccgcct ccctccccgc    180

ctcccccgcg cgccctcccc gcggaggtcc ctcccgtccg tcctcctgct ctctcctccg    240

cgggccgcat cgcccgggcc ggcgccgcgc gcgggggaag ctggcgggct gaggcgcccc    300

gctcttctcc tctgccccgg gcccgcgagg ccacgcgtcg ccgctcgaga gatgatgcag    360

gacgtgtcca gctcgccagt ctcgccggcc gacgacagcc tgagcaacag cgaggaagag    420

ccagaccggc agcagccgcc gagcggcaag cgcgggggac gcaagcggcg cagcagcagg    480

cgcagcgcgg gcggcggcgc ggggcccggc ggagccgcgg gtgggggcgt cggaggcggc    540

gacgagccgg gcagcccggc ccagggcaag cgcggcaaga agtctgcggg ctgtggcggc    600

ggcggcggcg cgggcggcgg cggcggcagc agcagcggcg gcgggagtcc gcagtcttac    660

gaggagctgc agacgcagcg ggtcatggcc aacgtgcggg agcgccagcg cacccagtcg    720

ctgaacgagg cgttcgccgc gctgcggaag atcatcccca cgctgccctc ggacaagctg    780

agcaagattc agaccctcaa gctggcggcc aggtacatcg acttcctcta ccaggtcctc    840

cagagcgacg agctggactc caagatggca agctgcagct atgtggctca cgagcggctc    900

agctacgcct tctcggtctg gaggatggag gggggcctggt ccatgtccgc gtcccactag    960

caggcggagc cccccacccc ctcagcaggg ccggagacct agatgtcatt gtttccagag   1020

aaggagaaaa tggacagtct agagactctg gagctggata actaaaaata aaaatatatg   1080

ccaaagattt tcttggaaat tagaagagca aaatccaaat tcaaagaaac agggcgtggg   1140

gcgcactttt aaaagagaaa gcgagacagg cccgtggaca gtgattccca gacgggcagc   1200

ggcaccatcc tcacacctct gcattctgat agaagtctga acagttgttt gtgttttttt   1260

ttttttttt tttgacgaag aatgttttta tttttatttt tttcatgcat gcattctcaa   1320

gaggtcgtgc caatcagcca ctgaaaggaa aggcatcact atggactttc tctattttaa   1380

aatggtaaca atcagaggaa ctataagaac acctttagaa ataaaaatac tgggatcaaa   1440

ctggcctgca aaaccatagt cagttaattc ttttttcat ccttcctctg aggggaaaaa   1500

caaaaaaaaa cttaaaatac aaaaaacaac attctattta tttattgagg acccatggta   1560

aaatgcaaat agatccggtg tctaaatgca ttcatatttt tatgattgtt ttgtaaatat   1620

ctttgtatat ttttctgcaa taaataaata taaaaaattt agagaaaaa              1669


<210> SEQ ID NO 14
<211> LENGTH: 160
<212> TYPE: PRT
```

<213> ORGANISM: Artificial sequence
<220> FEATURE:
<223> OTHER INFORMATION: Synthetic Polypeptide

<400> SEQUENCE: 14

```
Met Glu Glu Gly Ser Ser Ser Pro Val Ser Pro Val Asp Ser Leu Gly
1               5                   10                  15

Thr Ser Glu Glu Glu Leu Glu Arg Gln Pro Lys Arg Phe Gly Arg Lys
            20                  25                  30

Arg Arg Tyr Ser Lys Lys Ser Ser Glu Asp Gly Ser Pro Thr Pro Gly
        35                  40                  45

Lys Arg Gly Lys Lys Gly Ser Pro Ser Ala Gln Ser Phe Glu Glu Leu
    50                  55                  60

Gln Ser Gln Arg Ile Leu Ala Asn Val Arg Glu Arg Gln Arg Thr Gln
65                  70                  75                  80

Ser Leu Asn Glu Ala Phe Ala Ala Leu Arg Lys Ile Ile Pro Thr Leu
                85                  90                  95

Pro Ser Asp Lys Leu Ser Lys Ile Gln Thr Leu Lys Leu Ala Ala Arg
            100                 105                 110

Tyr Ile Asp Phe Leu Tyr Gln Val Leu Gln Ser Asp Glu Met Asp Asn
        115                 120                 125

Lys Met Thr Ser Cys Ser Tyr Val Ala His Glu Arg Leu Ser Tyr Ala
    130                 135                 140

Phe Ser Val Trp Arg Met Glu Gly Ala Trp Ser Met Ser Ala Ser His
145                 150                 155                 160
```

<210> SEQ ID NO 15
<211> LENGTH: 1409
<212> TYPE: DNA
<213> ORGANISM: Artificial sequence
<220> FEATURE:
<223> OTHER INFORMATION: Synthetic Polynucleotide

<400> SEQUENCE: 15

```
ctagagtttc caaaaaagtt agaataactt cctctcccgg agacctcggt tttgcacaag     60

ccggccttga aatcagagcc tttccagcaa ctccgagagc gtgtgctcgg cgaccgcggg    120

cttggccagc ggcgcgcgct cggcgccccg gcgcccccag ccccacgcgc gccgggcggg    180

cgccatggag gagggctcca gctcgcccgt gtcccccgtg gacagcctgg gcaccagcga    240

ggaggagctc gagaggcagc ccaagcgctt cggccggaag cggcgctaca gcaagaagtc    300

gagcgaagat ggcagcccga ccccgggcaa gcgcggcaag aagggcagcc ccagcgcgca    360

gtccttcgag gagctgcaga gccagcgcat cctggccaac gtgcgcgagc gccagcgcac    420

ccagtcgctc aacgaggcct tcgcggcgct gcgcaagatc atccccacgc tgccctctga    480

caagctgagc aagatccaga cgctcaagct ggccgccagg tacatagact tcctctacca    540

ggtcctgcag agcgacgaga tggacaataa gatgaccagc tgcagctacg tggcccacga    600

gcgcctcagc tacgccttct ccgtgtggcg catggagggc gcgtggtcca tgtccgcctc    660

ccactagcgc cgcgccaccc acctccggac cggcgcgcca gggctgtccg tcgcgtcggc    720

ggcgcaagtg gaattgggat gcattcgagt ctgtaacttc tgaaacctga acaacctcag    780

gaggcccccca cctctgccct ccaccagcgt cgagagaagg gacagcagtg acatcggaca    840

gaagacccgg gctcccgtcc tcccccagga cggtccccac ataggaaggg cactcccagc    900

cctcttgctg gtgacattgt catggtcatc ttgtttctgt ttggattttt cttctgggtc    960

ttatgtttgg ggggaggttt attctttctg aaaatgtcta gattcaggaa cacatttatg   1020
```

```
aggatttgga ttttgaattt gtatttccct ctaagtgcct tttttaatgt ctattttttt   1080

aataaaacag aaatgcattc ttgtacaatt ctgttgaaac tggaccaagg ctctcagaag   1140

aggacccccg agttccttcc cctcccccga gcctctgcat gattgtttca agtcagcctg   1200

gaattcttac tttcacgccg ctattctttt cctttctccg tgattgcttg gctagccatt   1260

taaaaaaaaa tattctctgt tcagtgtata tgttgcttgt ttgttttatt tattgagata   1320

tttttacaag ctaagtgact gcagtgtggc tgtgtatcct gctccccacc caggaaaaat   1380

aaagacgtcc gcgcagccat ggtctcccc                                     1409


<210> SEQ ID NO 16
<211> LENGTH: 8
<212> TYPE: PRT
<213> ORGANISM: Artificial sequence
<220> FEATURE:
<223> OTHER INFORMATION: Synthetic Polypeptide

<400> SEQUENCE: 16

Arg Arg Arg Arg Arg Arg Arg Arg
1               5


<210> SEQ ID NO 17
<211> LENGTH: 10
<212> TYPE: PRT
<213> ORGANISM: Artificial sequence
<220> FEATURE:
<223> OTHER INFORMATION: Synthetic Polypeptide

<400> SEQUENCE: 17

Arg Arg Arg Arg Arg Arg Arg Arg Arg Arg
1               5                   10


<210> SEQ ID NO 18
<211> LENGTH: 11
<212> TYPE: PRT
<213> ORGANISM: Artificial sequence
<220> FEATURE:
<223> OTHER INFORMATION: Synthetic Polypeptide

<400> SEQUENCE: 18

Arg Arg Arg Arg Arg Arg Arg Arg Arg Arg Arg
1               5                   10


<210> SEQ ID NO 19
<211> LENGTH: 12
<212> TYPE: PRT
<213> ORGANISM: Artificial sequence
<220> FEATURE:
<223> OTHER INFORMATION: Synthetic Polypeptide

<400> SEQUENCE: 19

Arg Arg Arg Arg Arg Arg Arg Arg Arg Arg Arg Arg
1               5                   10


<210> SEQ ID NO 20
<211> LENGTH: 13
<212> TYPE: PRT
<213> ORGANISM: Artificial sequence
<220> FEATURE:
<223> OTHER INFORMATION: Synthetic Polypeptide

<400> SEQUENCE: 20

Arg Arg Arg Arg Arg Arg Arg Arg Arg Arg Arg Arg Arg
1               5                   10
```

```
<210> SEQ ID NO 21
<211> LENGTH: 14
<212> TYPE: PRT
<213> ORGANISM: Artificial sequence
<220> FEATURE:
<223> OTHER INFORMATION: Synthetic Polypeptide

<400> SEQUENCE: 21

Arg Arg Arg Arg Arg Arg Arg Arg Arg Arg Arg Arg Arg Arg
1               5                   10


<210> SEQ ID NO 22
<211> LENGTH: 15
<212> TYPE: PRT
<213> ORGANISM: Artificial sequence
<220> FEATURE:
<223> OTHER INFORMATION: Synthetic Polypeptide

<400> SEQUENCE: 22

Arg Arg Arg Arg Arg Arg Arg Arg Arg Arg Arg Arg Arg Arg Arg
1               5                   10                  15


<210> SEQ ID NO 23
<211> LENGTH: 16
<212> TYPE: PRT
<213> ORGANISM: Artificial sequence
<220> FEATURE:
<223> OTHER INFORMATION: Synthetic Polypeptide

<400> SEQUENCE: 23

Arg Arg Arg Arg Arg Arg Arg Arg Arg Arg Arg Arg Arg Arg Arg Arg
1               5                   10                  15
```

PEPTIDE INHIBITORS OF TWIST

CROSS-REFERENCE TO RELATED APPLICATION

This application is a division of U.S. application Ser. No. 15/814,204, filed Nov. 15, 2017, now U.S. Pat. No. 10,646,540, which claims priority to U.S. Application No. 62/424,166 filed Nov. 18, 2016, the disclosures of which are incorporated by reference herein in their entireties.

STATEMENT AS TO RIGHTS TO INVENTIONS MADE UNDER FEDERALLY SPONSORED RESEARCH AND DEVELOPMENT

This invention was made with Government support under grant number P30 CA33572 awarded by the National Institutes of Health. The Government has certain rights in the invention.

REFERENCE TO A "SEQUENCE LISTING," A TABLE, OR A COMPUTER PROGRAM LISTING APPENDIX SUBMITTED AS AN ASCII FILE

The Sequence Listing written in file 048440-613D01US_SEQUENCE_LISTING_ST25.TXT, created on Apr. 7, 2020, 12,562 bytes, machine format IBM-PC, MS Windows operating system, is incorporated herein by reference.

BACKGROUND

The majority of cancer deaths are the result of tumor cells metastasizing beyond their original niche [1]. Disseminated disease is difficult to resect and frequently more heterogeneous than the primary tumor. Moreover, acquisition of drug resistance further complicates effective therapeutic approaches. In ovarian cancer in particular, late stage at discovery and drug resistance are major challenges [2,3], resulting in five year survival rates of approximately 25% [2,4]. Thus, a novel therapeutic addressing both metastasis and drug resistance is urgently needed.

A promising target for such an approach is the transcription factor TWIST1. TWIST1 expression and activity is essential in early development but suppressed in adults. However, many cancers reactivate TWIST1 expression [5-7]. In both the developmental and cancer settings, TWIST1 drives an epithelial to mesenchymal transition (EMT), in which cells alter their surface proteins to facilitate migration and invasion [6]. Enhanced cellular motility in turn gives rise to mesodermal tissues in embryogenesis and to metastases in the cancer setting [6,7]. Furthermore, TWIST1 has been implicated in a number of pro-progression phenotypes in cancer, including angiogenesis [8], increased cancer cell sternness [9,10], and survival signaling [11] (FIG. 1A).

TWIST1 has well-characterized transcription factor activity; its dimerization partners and binding site within target promoters have been elucidated previously [12,13]. Recently, more attention has been given to the Twist box or WR domain, comprised of the C-terminal twenty amino acids of the protein (FIG. 1B). The TWIST1 gene is well conserved evolutionarily, but this is especially true for the WR domain; 100% homology is preserved from human to xenopus (FIG. 1C). We have previously shown that the WR domain mediates a binding interaction between TWIST1 and the NF-κB subunit RELA, and that this interaction leads to transcriptional upregulation of the inflammatory cytokine interleukin 8 (IL-8) in a manner independent of TWIST1-DNA binding [14]. Furthermore, Piccinin et al. demonstrated a binding interaction between the WR domain and the C-terminus of the tumor suppressor p53, which led to p53 degradation [15]. Recently, it was revealed that the WR domain can also bind to the WR domain of a nearby TWIST1 heterodimer, thereby creating higher order complexes required for proper transcriptional regulation [13]. This finding sheds light on the discovery that altered TWIST1-mediated transcription was responsible for the inability of prostate cancer cells expressing truncated alleles of TWIST1 to metastasize in an in vivo model [16].

There is a need in the art for novel methods of treating cancer. The disclosure is directed to this, as well as other, important ends.

BRIEF SUMMARY

In a first aspect, there is provided a method of treating cancer in a subject in need thereof. The method includes administering to the subject a therapeutically effective amount of a TWIST inhibitor, where the TWIST inhibitor includes a TWIST peptide.

In another aspect, there is provided a method of inhibiting metastasis in a subject in need thereof. The method includes administering to the subject a therapeutically effective amount of a TWIST inhibitor, where the TWIST inhibitor includes a TWIST peptide.

In another aspect, there is provided a composition including a TWIST peptide or a nucleic acid encoding the TWIST peptide bound to a delivery vehicle, where the TWIST peptide includes a WR domain of TWIST1.

In another aspect, there is provided a fusion protein including a TWIST peptide covalently attached to a cell-penetrating peptide, where the TWIST peptide includes a WR domain of TWIST1.

In another aspect, there is provided a nucleic acid sequence encoding a fusion protein as disclosed herein.

BRIEF DESCRIPTION OF THE DRAWINGS

FIGS. 1A-1B. TWIST1 is a highly conserved bHLH class transcription factor with multiple functions. FIG. 1A: Carton depicting that TWIST1 functions in normal development and in small populations of adult stem cells, where it assists in wound healing. When reactivated in cancers, TWIST1 activates a transcriptional and protein binding program giving rise to EMT, and thus to metastases. Many studies have also linked re-expression of TWIST1 to the acquisition of drug resistance and an increase in stemness. Functions in normal tissue are shown in green; in cancer, in red. FIG. 1B: Human TWIST1 protein is 202 amino acids in length, with the N-terminal half of the protein being largely disordered. The C-terminal half consists of the basic DNA binding domain (labeled as "B"), helix-loop-helix dimerization domain (labeled as "HLH"), and the TWIST box or WR domain (labeled as "WR"), which has been shown to be a transactivation domain. FIG. 1C: The WR domain is especially well conserved throughout evolution, with 100% identity between human (*H. sapiens*), mouse (*M. musculus*), and frog (*X. laevis*), represented by SEQ ID NO:1. The central residues are present in all organisms, including *D. rerior* (represented by SEQ ID NO:2) and *D. melanogaster* (represented by SEQ ID NO:3), and for this reason, residues were selected for mutation.

FIG. 2A: Schematic representation of TWIST alleles used. Triple mutant contains W190A, R191A, and E193A mutations. FIG. 2B: Co-immunoprecipitation (Co-IP) reveals that single amino acid substitutions in the WR domain affect TWIST1-RELA binding, with the triple mutant producing a greater reduction in binding. FIG. 2C: Histogram depicting quantitation of Co-IP western blot. Graphed is the ratio of TWIST1 to RELA, each normalized to its input for each condition. FIG. 2D: Histogram depicting that dual luciferase assay demonstrates that IL-8 promoter driven luciferase activity, a surrogate for IL-8 activation by the TWIST1-RELA complex, is influenced by TWIST1 mutation. As seen in the Co-IP, single amino acid substitutions reduce FFluc expression by about 50% with respect to RELA alone, with the triple mutant producing a greater reduction. Graph represents firefly luciferase expression normalized to *renilla* luciferase for each condition. Error bars represent standard deviations of experiments done in triplicate. WT TWIST1 condition was used as the basis for statistical comparisons. Error bars, standard deviation. pGL3 lacking the IL-8 promoter was used as a negative control. *, $p<0.001$; **, $p<0.0001$.

FIG. 3A: Schematic representation of RELA alleles. FIG. 2B: Co-IP shows that expression of truncation mutants of either TWIST1 or RELA prevents most binding between TWIST1 and RELA. Co-expression of both truncation mutants further reduces binding, validating the truncated domains as required binding sites for their counterpart proteins. RELA Δ307 bands have been shown separate from WT due to difference in electrophoretic mobility on account of reduced size. FIG. 3C: Histogram depicting quantitation of Co-IP western blot. Graphed is the ratio of TWIST1 to RELA, each normalized to their respective inputs. FIG. 3D: Histogram depicting that dual luciferase assay reveals that while the Δ307 allele of RELA reduces TWIST1-mediated upregulation of IL-8 when compared to WT RELA, the same trend is seen in the absence of TWIST1. This suggests that the C-terminal portion of RELA is required not only for TWIST1 binding, but also for proper transcriptional activity. Graph represents firefly luciferase expression normalized to renilla luciferase for each condition. Error bars represent standard deviations of experiments done in triplicate. WT TWIST1+WT RELA condition was used as the basis for statistical comparisons. pGL3 lacking the IL-8 promoter was used as a negative control. Error bars, standard deviation. *, $p<0.001$; **, $p<0.0001$.

FIG. 4A: Schematic representation of GFP alleles used. GFP contains 23 amino acids encoded by the multiple cloning site of the vector at its C-terminus. GFP-WR contains the first two such amino acids (Leu-Glu encoded by XhoI restriction site), followed by the 20 amino acids of the WR domain. Thus, the two alleles have indistinguishable molecular weights. FIG. 4B: Photomicrographs depicting that GFP and GFP-WR are expressed at similar levels and in similar patterns in HEK-293 cells. Strong cytoplasmic signal reveals that GFP is being expressed primarily in this compartment. Scale bar, 100 μm. FIG. 4C: Co-IP with RELA pulldown reveals that in the presence of increasing GFP-WR expression, TWIST1-RELA binding is reduced in a dose-dependent manner. FIG. 4D: Histogram depicting that Co-IP with GFP pulldown reveals that increasing GFP-WR dose results in more TWIST1 co-precipitated with GFP. FIG. 4E: Histogram depicts that dual luciferase assay demonstrates that as seen in the RELA CoIP, there is a dose dependent drop in IL-8 driven luciferase expression with increasing dose of GFP-WR inhibitor. Graph represents firefly luciferase expression normalized to renilla luciferase for each condition. Error bars represent standard deviations of experiments done in triplicate. GFP without GFP-WR condition was used as the basis for statistical comparisons. pGL3 lacking the IL-8 promoter was used as a negative control. Error bars, standard deviation. ****, $p<0.0001$.

FIG. 5A: Histogram depicting that fractionation experiments reveal a slight increase in TWIST1 localization to the cytoplasm with increasing levels of GFP-WR. FIG. 5B: Western blotting shows that despite a greater proportion of TWIST1 being localized outside the nucleus when GFP-WR is present, most is cytoplasmic across all conditions. Furthermore, TWIST1 and GFP levels decrease as the ratio of GFP-WR to GFP is increased. This observation suggests proteasomal degradation of these proteins. FIG. 5C: Histograms depicting that treating cells with the proteasome inhibitor MG132 partially rescues TWIST1 (left panel) and GFP (right panel) from degradation. FIG. 5B: Histogram depicting that dual luciferase assay demonstrates that MG132 treatment increases IL-8 driven FFluc expression. Graph represents firefly luciferase expression normalized to renilla luciferase for each condition. Error bars represent standard deviations of experiments done in triplicate. GFP without GFP-WR or MG132 was used as the basis for statistical comparisons. pGL3 lacking the IL-8 promoter was used as a negative control. Error bars, standard deviation. *, $p<0.05$.

DETAILED DESCRIPTION

Definitions

Figure 2A:
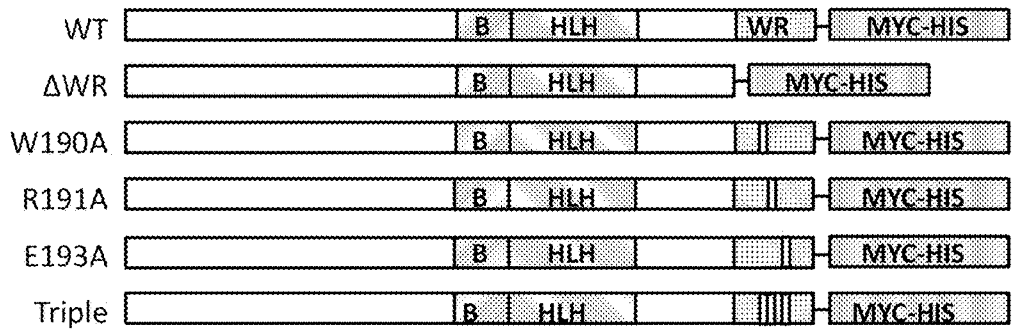
FIGS. 2A-2D. Mutation of the WR domain abrogates TWIST1 interaction with RELA.

While various embodiments and aspects of the present invention are shown and described herein, it will be obvious to those skilled in the art that such embodiments and aspects are provided by way of example only. Numerous variations, changes, and substitutions will now occur to those skilled in the art without departing from the invention. It should be understood that various alternatives to the embodiments of the invention described herein may be employed in practicing the invention.

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them unless specified otherwise.

The use of a singular indefinite or definite article (e.g., “a,” “an,” “the,” etc.) in this disclosure and in the following claims follows the traditional approach in patents of meaning “at least one” unless in a particular instance it is clear from context that the term is intended in that particular instance to mean specifically one and only one. Likewise, the term “comprising” is open ended, not excluding additional items, features, components, etc. References identified herein are expressly incorporated herein by reference in their entireties unless otherwise indicated.

The terms "comprise," "include," and "have," and the derivatives thereof, are used herein interchangeably as comprehensive, open-ended terms. For example, use of "comprising," "including," or "having" means that whatever element is comprised, had, or included, is not the only element encompassed by the subject of the clause that contains the verb.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics which are not found in nature.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The terms "polypeptide," "peptide" and "protein" are used interchangeably herein to refer to a polymer of amino acid residues, wherein the polymer may In embodiments be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers. A "fusion protein" refers to a chimeric protein encoding two or more separate protein sequences that are recombinantly expressed as a single moiety.

As may be used herein, the terms "nucleic acid," "nucleic acid molecule," "nucleic acid oligomer," "oligonucleotide," "nucleic acid sequence," "nucleic acid fragment" and "polynucleotide" are used interchangeably and are intended to include, but are not limited to, a polymeric form of nucleotides covalently linked together that may have various lengths, either deoxyribonucleotides or ribonucleotides, or analogs, derivatives or modifications thereof. Different polynucleotides may have different three-dimensional structures, and may perform various functions, known or unknown. Non-limiting examples of polynucleotides include a gene, a gene fragment, an exon, an intron, intergenic DNA (including, without limitation, heterochromatic DNA), messenger RNA (mRNA), transfer RNA, ribosomal RNA, a ribozyme, cDNA, a recombinant polynucleotide, a branched polynucleotide, a plasmid, a vector, isolated DNA of a sequence, isolated RNA of a sequence, a nucleic acid probe, and a primer. Polynucleotides useful in the methods of the invention may comprise natural nucleic acid sequences and variants thereof, artificial nucleic acid sequences, or a combination of such sequences.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

"Conservatively modified variants" applies to both amino acid and nucleic acid sequences. With respect to particular nucleic acid sequences, "conservatively modified variants" refers to those nucleic acids that encode identical or essentially identical amino acid sequences. Because of the degeneracy of the genetic code, a number of nucleic acid sequences will encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: (1) Alanine (A), Glycine (G); (2) Aspartic acid (D), Glutamic acid (E); (3) Asparagine (N), Glutamine (Q); (4) Arginine (R), Lysine (K); (5) Isoleucine (I), Leucine (L), Methionine (M), Valine (V); (6) Phenylalanine (F), Tyrosine (Y), Tryptophan (W); (7) Serine (S), Threonine (T); and (8) Cysteine (C), Methionine (M) (see, e.g., Creighton, *Proteins* (1984)).

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site http://www.ncbi.nlm.nih.gov/BLAST/ or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

An amino acid or nucleotide base "position" is denoted by a number that sequentially identifies each amino acid (or nucleotide base) in the reference sequence based on its position relative to the N-terminus (or 5'-end). Due to deletions, insertions, truncations, fusions, and the like that must be taken into account when determining an optimal alignment, in general the amino acid residue number in a test sequence determined by simply counting from the N-terminus will not necessarily be the same as the number of its corresponding position in the reference sequence. For example, in a case where a variant has a deletion relative to an aligned reference sequence, there will be no amino acid in the variant that corresponds to a position in the reference sequence at the site of deletion. Where there is an insertion in an aligned reference sequence, that insertion will not correspond to a numbered amino acid position in the reference sequence. In the case of truncations or fusions there can be stretches of amino acids in either the reference or aligned sequence that do not correspond to any amino acid in the corresponding sequence.

The terms "numbered with reference to" or "corresponding to," when used in the context of the numbering of a given amino acid or polynucleotide sequence, refers to the numbering of the residues of a specified reference sequence when the given amino acid or polynucleotide sequence is compared to the reference sequence.

The term "probe" or "primer", as used herein, is defined to be one or more nucleic acid fragments whose specific hybridization to a sample can be detected. A probe or primer can be of any length depending on the particular technique it will be used for. For example, PCR primers are generally between 10 and 40 nucleotides in length, while nucleic acid probes for, e.g., a Southern blot, can be more than a hundred nucleotides in length. The probe may be unlabeled or labeled as described below so that its binding to the target or sample can be detected. The probe can be produced from a source of nucleic acids from one or more particular (preselected) portions of a chromosome, e.g., one or more clones, an isolated whole chromosome or chromosome fragment, or a collection of polymerase chain reaction (PCR) amplification products. The length and complexity of the nucleic acid fixed onto the target element is not critical to the invention. One of skill can adjust these factors to provide optimum hybridization and signal production for a given hybridization procedure, and to provide the required resolution among different genes or genomic locations.

The probe may also be isolated nucleic acids immobilized on a solid surface (e.g., nitrocellulose, glass, quartz, fused silica slides), as in an array. In some embodiments, the probe may be a member of an array of nucleic acids as described, for instance, in WO 96/17958. Techniques capable of producing high density arrays can also be used for this purpose (see, e.g., Fodor (1991) Science 767-773; Johnston (1998) Curr. Biol. 8: R171-R174; Schummer (1997) Biotechniques 23: 1087-1092; Kern (1997) Biotechniques 23: 120-124; U.S. Pat. No. 5,143,854).

The phrase "selectively (or specifically) hybridizes to" refers to the binding, duplexing, or hybridizing of a molecule only to a particular nucleotide sequence with a higher affinity, e.g., under more stringent conditions, than to other nucleotide sequences (e.g., total cellular or library DNA or RNA).

The phrase "stringent hybridization conditions" refers to conditions under which a nucleic acid will hybridize to its target sequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, stringent hybridization conditions are selected to be about 5-10° C. lower than the thermal melting point (Tm) for the specific sequence at a defined ionic strength pH. The Tm is the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent hybridization conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and Current Protocols in Molecular Biology, ed. Ausubel, et al., John Wiley & Sons.

As used herein, the term "conjugate" refers to the association between atoms or molecules. The association can be direct or indirect. For example, a conjugate between a first moiety (e.g., nucleic acid moiety) and a second moiety (peptide moiety) provided herein can be direct, e.g., by covalent bond, or indirect, e.g., by non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like).

In embodiments, conjugates are formed using conjugate chemistry including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, Advanced Organic Chemistry, 3rd Ed., John Wiley & Sons, New York, 1985; Hermanson, Bioconjugate Techniques, Academic Press, San Diego, 1996; and Feeney et al., Modification of Proteins; Advances in Chemistry Series, Vol. 198, American Chemical Society, Washington, D.C., 1982. In embodiments, the first moiety (e.g., polyamine moiety) is non-covalently attached to the second moiety (peptide moiety) through a non-covalent chemical reaction between a component of the first moiety (e.g., polyamine moiety) and a component of the second moiety (peptide moiety). In other embodiments, the first moiety (e.g., polyamine moiety) includes one or more reactive moieties, e.g., a covalent reactive moiety, as described herein (e.g., alkyne, azide, maleimide or thiol reactive moiety). In other embodiments, the first moiety (e.g., polyamine moiety) includes a linker with one or more reactive moieties, e.g., a covalent reactive moiety, as described herein (e.g., alkyne, azide, maleimide or thiol reactive moiety). In other embodiments, the second moiety (peptide moiety) includes one or more reactive moieties, e.g., a covalent reactive moiety, as described herein (e.g., alkyne, azide, maleimide or thiol reactive moiety). In other embodiments, the second moiety (peptide moiety) includes a linker with one or more reactive moieties, e.g., a covalent reactive moiety, as described herein (e.g., alkyne, azide, maleimide or thiol reactive moiety).

For specific proteins described herein (e.g., TWIST, including TWIST1 and TWIST2), the named protein includes any of the protein's naturally occurring forms, or variants that maintain the protein transcription factor activity (e.g., within at least 50%, 80%, 90%, 95%, 96%, 97%, 98%, 99% or 100% activity compared to the native protein). In some embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In other embodiments, the protein is the protein as identified by its NCBI sequence reference. In other embodiments, the protein is the protein as identified by its NCBI sequence reference or functional fragment thereof.

A "TWIST1 protein" as referred to herein includes any of the recombinant or naturally-occurring forms of the protein of Twist Family BHLH Transcription Factor 1 (TWIST1), homologs or variants thereof that maintain TWIST1 protein activity (e.g. within at least 50%, 80%, 90%, 95%, 96%, 97%, 98%, 99% or 100% activity compared to TWIST1). In embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring TWIST1 polypeptide (NCBI reference number: NP_000465.1 or Gene ID: GI:4507741).

A "TWIST2 protein" as referred to herein includes any of the recombinant or naturally-occurring forms of the protein of Twist Family BHLH Transcription Factor 2 (TWIST2), homologs or variants thereof that maintain TWIST2 protein activity (e.g. within at least 50%, 80%, 90%, 95%, 96%, 97%, 98%, 99% or 100% activity compared to TWIST2). In embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring TWIST2 polypeptide (NCBI reference number: NP_001258822.1 or Gene ID:429325228).

A "TWIST peptide" as used herein refers to a polypeptide that is derived from a TWIST1 protein or a TWIST2 protein. In embodiments, the TWIST peptide is derived from a TWIST1 protein. In embodiments, the TWIST peptide is derived from a TWIST1 carboxy-terminal WR (Trp-Arg) domain (also referred to herein as a WR domain). In embodiments, the TWIST peptide retains at least in part a biological function of a TWIST1 carboxy-terminal WR domain. For example, in embodiments the TWIST peptide retains the ability of a TWIST1 carboxy-terminal WR domain to: bind the NF-κB subunit RELA (e.g. bind competitively with TWIST 1 or TWIST1 carboxy-terminal WR domain to the NF-κB subunit RELA); increase transcriptional upregulation of the inflammatory cytokine interleukin 8 (IL-8) in a cell (relative to the absence of the TWIST 1 peptide); bind to p53 (e.g. bind competitively with TWIST 1 or TWIST1 carboxy-terminal WR domain to p53); degrade p53 in a cell (relative to the absence of the TWIST 1 peptide); bind to the WR domain of a different TWIST1 protein (e.g. bind competitively with TWIST1 or TWIST1 carboxy-terminal WR domain to the WR domain of a different TWIST1 protein); disrupt higher order TWIST1 complex formation in vitro or in a cell; decrease TWIST1 functions associated with cancer (relative to the absence of the TWIST 1 peptide); and/or abrogate TWIST1 activity in vitro or in a cell (relative to the absence of the TWIST 1 peptide). In embodiments, a TWIST peptide is about at least 10 amino acids (e.g., at least 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 amino acids) in length. In embodiments, a TWIST peptide includes an amino acid sequence of SEQ ID NO: 1. In embodiments, a TWIST peptide includes an amino acid sequence having at least 50%, 80%, 90%, 95%, 96%, 97%, 98%, 99% or 100% sequence identity to SEQ ID NO: 1.

As used herein, the term "vector" refers to a nucleic acid molecule capable of transporting another nucleic acid to which it has been linked. One type of vector is a "plasmid", which refers to a linear or circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions. Additionally, some viral vectors are capable of targeting a particular cells type either specifically or non-specifically. Replication-incompetent viral vectors or replication-defective viral vectors refer to viral vectors that are capable of infecting their target cells and delivering their viral payload, but then fail to continue the typical lytic pathway that leads to cell lysis and death.

The compositions described herein can be purified. Purified compositions are at least about 60% by weight (dry weight) the compound of interest. Preferably, the preparation is at least about 75%, more preferably at least about 90%, and most preferably at least about 99% or higher by weight the compound of interest. Purity is measured by any appropriate standard method, for example, by High-performance liquid chromatography, polyacrylamide gel electrophoresis.

The term "isolated", when applied to a nucleic acid or protein, denotes that the nucleic acid or protein is essentially free of other cellular components with which it is associated in the natural state. It can be, for example, in a homogeneous state and may be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaryotic cells. Prokaryotic cells include but are not limited to bacteria. Eukaryotic cells include but are not limited to yeast cells and cells derived from plants and animals, for example mammalian, insect (e.g., *spodoptera*) and human cells.

The terms "inhibitor," "repressor" or "antagonist" or "downregulator" interchangeably refer to a substance that results in a detectably lower expression or activity level as compared to a control. The inhibited expression or activity can be 10%, 20%, 30%, 40%, 50%, 60%, 70%, 80%, 90% or less than that in a control. In certain instances, the inhibition is 1.5-fold, 2-fold, 3-fold, 4-fold, 5-fold, 10-fold, or more in comparison to a control. An "inhibitor" is a peptide, siRNA, (e.g., shRNA, miRNA, snoRNA), compound or small molecule that inhibits cellular function (e.g., replication) e.g., by binding, partially or totally blocking stimulation, decrease, prevent, or delay activation, or inactivate, desensitize, or down-regulate signal transduction, gene expression or enzymatic activity necessary for protein activity. A "TWIST inhibitor" refers to a substance that results in a detectably lower expression of TWIST (TWIST1, TWIST2 or both) genes or TWIST (TWIST1, TWIST2 or both) proteins or lower activity level of TWIST (TWIST1, TWIST2 or both) proteins as compared to those levels without such substance. In some embodiments, a TWIST inhibitor is an inhibitor for both TWIST1 and TWIST2. In some embodiments, a TWIST inhibitor is a TWIST peptide. In some embodiments, a TWIST inhibitor is a composition (e.g., a TWIST peptide bound to a delivery vehicle or a fusion protein including a TWIST peptide) described herein. In some embodiments, a TWIST inhibitor is a pharmaceutical composition described herein.

A "pharmaceutical composition" is a formulation containing the composition (e.g., a TWIST peptide, a TWIST peptide bound to a delivery vehicle or a fusion protein including a TWIST peptide) described herein in a form suitable for administration to a subject. In embodiments, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed nucleic acid) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this invention include powders, sprays, ointments, pastes, creams, lotions, gels, solutions, patches and inhalants. In embodiments, the active ingredient (e.g., a TWIST peptide, a TWIST peptide bound to a delivery vehicle or a fusion protein including a TWIST peptide) described herein is mixed under sterile conditions with a pharmaceutically acceptable carrier, and with any preservatives, buffers, or propellants that are required.

As used herein, the phrase "pharmaceutically acceptable" refers to those compounds, anions, cations, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient. A thorough discussion of pharmaceutically acceptable excipients is available in Remington's Pharmaceutical Sciences (Mack Pub. Co., N.J. 1991). Pharmaceutically acceptable excipients in therapeutic compositions may contain liquids such as water, saline, glycerol and ethanol. Additionally, auxiliary substances, such as wetting or emulsifying agents, pH buffering substances, and the like, may be present in such vehicles.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), and transmucosal administration.

Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

Pharmaceutical compositions can also include large, slowly metabolized macromolecules such as proteins, polysaccharides such as chitosan, polylactic acids, polyglycolic acids and copolymers (such as latex functionalized Sepharose™, agarose, cellulose, and the like), polymeric amino acids, amino acid copolymers, and lipid aggregates (such as oil droplets or liposomes). Additionally, these carriers can function as immunostimulating agents (i.e., adjuvants).

Suitable formulations for rectal administration include, for example, suppositories, which consist of the packaged nucleic acid with a suppository base. Suitable suppository bases include natural or synthetic triglycerides or paraffin hydrocarbons. In addition, it is also possible to use gelatin rectal capsules which consist of a combination of the compound of choice with a base, including, for example, liquid triglycerides, polyethylene glycols, and paraffin hydrocarbons.

Formulations suitable for parenteral administration, such as, for example, by intraarticular (in the joints), intravenous, intramuscular, intratumoral, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. Parenteral administration, oral administration, and intravenous administration are the preferred methods of administration. The formulations of compounds can be presented in unit-dose or multi-dose sealed containers, such as ampules and vials.

Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

A pharmaceutical composition of the invention can be administered to a subject in many of the well-known methods currently used for chemotherapeutic treatment. For example, for treatment of cancers, a composition of the invention may be injected directly into tumors, injected into the blood stream or body cavities or taken orally or applied through the skin with patches. The dose chosen should be sufficient to constitute effective treatment but not so high as to cause unacceptable side effects. The state of the disease condition (e.g., cancer, precancer, and the like) and the health of the patient should preferably be closely monitored during and for a reasonable period after treatment.

As used herein, "monotherapy" refers to the administration of a single active or therapeutic compound to a subject in need thereof. Preferably, monotherapy will involve administration of a therapeutically effective amount of an active composition (e.g., a TWIST peptide, a TWIST peptide bound to a delivery vehicle, a fusion protein including a TWIST peptide, or any composition described herein). For example, described herein can be a cancer monotherapy with one of compositions described herein administered to a subject in need of for treatment of cancer. Monotherapy may be contrasted with combination therapy, in which a combination of multiple active compositions (e.g., multiple compositions described herein) are administered, preferably with each component of the combination present in a therapeutically effective amount. Monotherapy with a composition described herein may be more effective than combination therapy in inducing a desired biological effect.

As used herein, "combination therapy" or "co-therapy" or "co-administration" includes the administration of a composition of the present invention and at least a second agent as part of a specific treatment regimen intended to provide the beneficial effect from the co-action of these therapeutic agents. The beneficial effect of the combination may include, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). "Combination therapy" may be, but generally is not, intended to encompass the administration of two or more of these therapeutic agents as part of separate monotherapy regimens that incidentally and arbitrarily result in the combinations of the present invention.

In some embodiments, co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In other embodiments, the active agents can be formulated separately. In another embodiment, the active and/or adjunctive agents may be linked or conjugated to one another. In some embodiments, the compounds described herein may be combined with treatments for cancer (e.g. prostate cancer, castration-resistant prostate cancer, breast cancer, triple negative breast cancer, glioblastoma, ovarian cancer, lung cancer, squamous cell carcinoma (e.g head, neck, or esophagus), colorectal cancer, leukemia, acute myeloid leukemia, lymphoma, B cell lymphoma, or multiple myeloma) such as surgery or with other treatments known to be useful in treating viral disease (e.g. herpesvirus infection associated disease or hepatitis virus infection associated disease or HIV infection associated disease).

"Combination therapy" is intended to embrace administration of these therapeutic agents in a sequential manner, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical.

"Combination therapy" also embraces the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

A composition of the present invention may be administered in combination with a second chemotherapeutic agent. The second chemotherapeutic agent (also referred to as an anti-neoplastic agent or anti-proliferative agent) can be an alkylating agent; an antibiotic; an anti-metabolite; a detoxifying agent; an interferon; a polyclonal or monoclonal antibody; an EGFR inhibitor; a HER2 inhibitor; a histone deacetylase inhibitor; a hormone; a mitotic inhibitor; an MTOR inhibitor; a multi-kinase inhibitor; a serine/threonine kinase inhibitor; a tyrosine kinase inhibitors; a VEGF/VEGFR inhibitor; a taxane or taxane derivative, an aromatase inhibitor, an anthracycline, a microtubule targeting drug, a topoisomerase poison drug, an inhibitor of a molecular target or enzyme (e.g., a kinase or a protein methyltransferase), a cytidine analogue drug or any chemotherapeutic, anti-neoplastic or anti-proliferative agent listed in www.cancer.org/docroot/cdg/cdg_0.asp.

"Anti-cancer agent" is used in accordance with its plain ordinary meaning and refers to a composition (e.g. compound, drug, antagonist, inhibitor, modulator) having antineoplastic properties or the ability to inhibit the growth or proliferation of cells. In embodiments, an anti-cancer agent is a chemotherapeutic. In embodiments, an anti-cancer agent is an agent identified herein having utility in methods of treating cancer. In embodiments, an anti-cancer agent is an agent approved by the FDA or similar regulatory agency of a country other than the USA, for treating cancer.

The anti-cancer agents set forth below are for illustrative purposes and not intended to be limiting. The present invention includes at least one anti-cancer agent selected from the lists below. The present invention can include more than one anti-cancer agent, e.g., two, three, four, or five anti-cancer agents such that the composition of the present invention can perform its intended function.

In embodiments, the anticancer agent is a compound that affects histone modifications, such as an HDAC inhibitor. In certain embodiments, an anticancer agent is selected from the group consisting of chemotherapeutics (such as 2CdA, 5-FU, 6-Mercaptopurine, 6-TG, Abraxane™ Accutane®, Actinomycin-D, Adriamycin®, Alimta®, all-trans retinoic acid, amethopterin, Ara-C, Azacitadine, BCNU, Blenoxane®, Camptosar®, CeeNU®, Clofarabine, Clolar™, Cytoxan®, daunorubicin hydrochloride, DaunoXome®, Dacogen®, DIC, Doxil®, Ellence®, Eloxatin®, Emcyt®, etoposide phosphate, Fludara®, FUDR®, Gemzar®, Gleevec®, hexamethylmelamine, Hycamtin®, Hydrea®, Idamycin®, Ifex®, ixabepilone, Ixempra®, L-asparaginase, Leukeran®, liposomal Ara-C, L-PAM, Lysodren, Matulane®, mithracin, Mitomycin-C, Myleran®, Navelbine®, Neutrexin®, nilotinib, Nipent®, Nitrogen Mustard, Novantrone®, Oncaspar®, Panretin®, Paraplatin®, Platinol®, prolifeprospan 20 with carmustine implant, Sandostatin®, Targretin®, Tasigna®, Taxotere®, Temodar®, TESPA, Trisenox®, Valstar®, Velban®, Vidaza™, vincristine sulfate, VM 26, Xeloda® and Zanosar®); biologics (such as Alpha Interferon, *Bacillus* Calmette-Guerin, Bexxar®, Campath®, Ergamisol®, Erlotinib, Herceptin®, Interleukin-2, Iressa®, lenalidomide, Mylotarg®, Ontak®, Pegasys®, Revlimid®, Rituxan®, Tarceva™, Thalomid®, Tykerb®, Velcade® and Zevalin™); corticosteroids, (such as dexamethasone sodium phosphate, DeltaSone® and Delta-Cortef®); hormonal therapies (such as Arimidex®, Aromasin®, Casodex®, Cytadren®, Eligard®, Eulexin®, Evista®, Faslodex®, Femara®, Halotestin®, Megace®, Nilandron®, Nolvadex®, Plenaxis™ and Zoladex®); and radiopharmaceuticals (such as Iodotope®, Metastron®, Phosphocol® and Samarium SM-153).

In embodiments, the anti-cancer agent is a chemotherapeutic agent (also referred to as an anti-neoplastic agent or anti-proliferative agent), selected from the group including an alkylating agent; an antibiotic; an anti-metabolite; a detoxifying agent; an interferon; a polyclonal or monoclonal antibody; an EGFR inhibitor; a HER2 inhibitor; a histone deacetylase inhibitor; a hormone; a mitotic inhibitor; an MTOR inhibitor; a multi-kinase inhibitor; a serine/threonine kinase inhibitor; a tyrosine kinase inhibitors; a VEGF/VEGFR inhibitor; a taxane or taxane derivative, an aromatase inhibitor, an anthracycline, a microtubule targeting drug, a topoisomerase poison drug, an inhibitor of a molecular target or enzyme (e.g., a kinase or a protein methyltransferase), a cytidine analogue drug or any chemotherapeutic, anti-neoplastic or anti-proliferative agent listed in www.cancer.org/docroot/cdg/cdg_0.asp.

Exemplary alkylating agents include, but are not limited to, cyclophosphamide (Cytoxan; Neosar); chlorambucil (Leukeran); melphalan (Alkeran); carmustine (BiCNU); busulfan (Busulfex); lomustine (CeeNU); dacarbazine (DTIC-Dome); oxaliplatin (Eloxatin); carmustine (Gliadel); ifosfamide (Ifex); mechlorethamine (Mustargen); busulfan (Myleran); carboplatin (Paraplatin); cisplatin (CDDP; Platinol); temozolomide (Temodar); thiotepa (Thioplex); bendamustine (Treanda); or streptozocin (Zanosar).

Exemplary antibiotics include, but are not limited to, doxorubicin (Adriamycin); doxorubicin liposomal (Doxil); mitoxantrone (Novantrone); bleomycin (Blenoxane); daunorubicin (Cerubidine); daunorubicin liposomal (DaunoXome); dactinomycin (Cosmegen); epirubicin (Ellence); idarubicin (Idamycin); plicamycin (Mithracin); mitomycin (Mutamycin); pentostatin (Nipent); or valrubicin (Valstar).

Exemplary anti-metabolites include, but are not limited to, fluorouracil (Adrucil); capecitabine (Xeloda); hydroxyurea (Hydrea); mercaptopurine (Purinethol); pemetrexed (Alimta); fludarabine (Fludara); nelarabine (Arranon); cladribine (Cladribine Novaplus); clofarabine (Clolar); cytarabine (Cytosar-U); decitabine (Dacogen); cytarabine liposomal (DepoCyt); hydroxyurea (Droxia); pralatrexate (Folotyn); floxuridine (FUDR); gemcitabine (Gemzar); cladribine (Leustatin); fludarabine (Oforta); methotrexate (MTX; Rheumatrex); methotrexate (Trexall); thioguanine (Tabloid); TS-1 or cytarabine (Tarabine PFS).

Exemplary detoxifying agents include, but are not limited to, amifostine (Ethyol) or mesna (Mesnex).

Exemplary interferons include, but are not limited to, interferon alfa-2b (Intron A) or interferon alfa-2a (Roferon-A).

Exemplary polyclonal or monoclonal antibodies include, but are not limited to, trastuzumab (Herceptin); ofatumumab (Arzerra); bevacizumab (Avastin); rituximab (Rituxan); cetuximab (Erbitux); panitumumab (Vectibix); tositumomab/iodine131 tositumomab (Bexxar); alemtuzumab (Campath); ibritumomab (Zevalin; In-111; Y-90 Zevalin); gemtuzumab (Mylotarg); eculizumab (Soliris) ordenosumab.

Exemplary EGFR inhibitors include, but are not limited to, gefitinib (Iressa); lapatinib (Tykerb); cetuximab (Erbitux); erlotinib (Tarceva); panitumumab (Vectibix); PKI-166; canertinib (CI-1033); matuzumab (Emd7200) or EKB-569.

Exemplary HER2 inhibitors include, but are not limited to, trastuzumab (Herceptin); lapatinib (Tykerb) or AC-480.

Exemplary Histone Deacetylase Inhibitors include, but are not limited to, vorinostat (Zolinza).

Exemplary hormones include, but are not limited to, tamoxifen (Soltamox; Nolvadex); raloxifene (Evista); megestrol (Megace); leuprolide (Lupron; Lupron Depot; Eligard; Viadur); fulvestrant (Faslodex); letrozole (Femara); triptorelin (Trelstar LA; Trelstar Depot); exemestane (Aromasin); goserelin (Zoladex); bicalutamide (Casodex); anastrozole (Arimidex); fluoxymesterone (Androxy; Halotestin); medroxyprogesterone (Provera; Depo-Provera); estramustine (Emcyt); flutamide (Eulexin); toremifene (Fareston); degarelix (Firmagon); nilutamide (Nilandron); abarelix (Plenaxis); or testolactone (Teslac).

Exemplary mitotic inhibitors include, but are not limited to, paclitaxel (Taxol; Onxol; Abraxane); docetaxel (Taxotere); vincristine (Oncovin; Vincasar PFS); vinblastine (Velban); etoposide (Toposar; Etopophos; VePesid); teniposide (Vumon); ixabepilone (Ixempra); nocodazole; epothilone; vinorelbine (Navelbine); camptothecin (CPT); irinotecan (Camptosar); topotecan (Hycamtin); amsacrine or lamellarin D (LAM-D).

Exemplary MTOR inhibitors include, but are not limited to, everolimus (Afinitor) or temsirolimus Torisel); rapamune, ridaforolimus; or AP23573.

Exemplary multi-kinase inhibitors include, but are not limited to, sorafenib (Nexavar); sunitinib (Sutent); BMW 2992; E7080; Zd6474; PKC-412; motesanib; or AP24534.

Exemplary serine/threonine kinase inhibitors include, but are not limited to, ruboxistaurin; eril/easudil hydrochloride; flavopiridol; Pkc412; bryostatin; KAI-9803; SF1126; or PD 332991.

Exemplary tyrosine kinase inhibitors include, but are not limited to, erlotinib (Tarceva); gefitinib (Iressa); imatinib (Gleevec); sorafenib (Nexavar); sunitinib (Sutent); trastuzumab (Herceptin); bevacizumab (Avastin); rituximab (Rituxan); lapatinib (Tykerb); cetuximab (Erbitux); panitumumab (Vectibix); everolimus (Afinitor); alemtuzumab (Campath); gemtuzumab (Mylotarg); temsirolimus (Torisel); pazopanib (Votrient); dasatinib (Sprycel); nilotinib (Tasigna); vatalanib (Ptk787; ZK222584); WHI-P154; WHI-P131; AC-220; or AMG888.

Exemplary VEGF/VEGFR inhibitors include, but are not limited to, bevacizumab (Avastin); sorafenib (Nexavar); sunitinib (Sutent); ranibizumab; pegaptanib; or vandetinib.

Exemplary microtubule targeting drugs include, but are not limited to, paclitaxel, docetaxel, vincristine, vinblastin, nocodazole, epothilones and navelbine.

Exemplary topoisomerase poison drugs include, but are not limited to, teniposide, etoposide, adriamycin, camptothecin, daunorubicin, dactinomycin, mitoxantrone, amsacrine, epirubicin and idarubicin.

Exemplary taxanes or taxane derivatives include, but are not limited to, paclitaxel and docetaxol.

Exemplary general chemotherapeutic, anti-neoplastic, anti-proliferative agents include, but are not limited to, altretamine (Hexalen); isotretinoin (Accutane; Amnesteem; Claravis; Sotret); tretinoin (Vesanoid); azacitidine (Vidaza); bortezomib (Velcade) asparaginase (Elspar); levamisole (Ergamisol); mitotane (Lysodren); procarbazine (Matulane); pegaspargase (Oncaspar); denileukin diftitox (Ontak); porfimer (Photofrin); aldesleukin (Proleukin); lenalidomide (Revlimid); bexarotene (Targretin); thalidomide (Thalomid); temsirolimus (Torisel); arsenic trioxide (Trisenox); verteporfin (Visudyne); mimosine (Leucenol); (1M tegafur—0.4 M 5-chloro-2,4-dihydroxypyrimidine—1 M potassium oxonate), or lovastatin.

In embodiments, the anti-cancer agent is a chemotherapeutic agent or a cytokine such as G-CSF (granulocyte colony stimulating factor).

In embodiments, the anti-cancer agents can be standard chemotherapy combinations such as, but not restricted to, CMF (cyclophosphamide, methotrexate and 5-fluorouracil), CAF (cyclophosphamide, adriamycin and 5-fluorouracil), AC (adriamycin and cyclophosphamide), FEC (5-fluorouracil, epirubicin, and cyclophosphamide), ACT or ATC (adriamycin, cyclophosphamide, and paclitaxel), rituximab, Xeloda (capecitabine), Cisplatin (CDDP), Carboplatin, TS-1 (tegafur, gimestat and otastat potassium at a molar ratio of 1:0.4:1), Camptothecin-11 (CPT-11, Irinotecan or Camptosar™), CHOP (cyclophosphamide, hydroxydaunorubicin, oncovin, and prednisone or prednisolone), R-CHOP (rituximab, cyclophosphamide, hydroxydaunorubicin, oncovin, prednisone or prednisolone), or CMFP (cyclophosphamide, methotrexate, 5-fluorouracil and prednisone).

In embodiments, the anti-cancer agents can be an inhibitor of an enzyme, such as a receptor or non-receptor kinase. Receptor and non-receptor kinases are, for example, tyrosine kinases or serine/threonine kinases. Kinase inhibitors described herein are small molecules, polynucleic acids, polypeptides, or antibodies. Exemplary kinase inhibitors include, but are not limited to, Bevacizumab (targets VEGF), BMW 2992 (targets EGFR and Erb2), Cetuximab/Erbitux (targets Erb1), Imatinib/Gleevic (targets Bcr-Abl), Trastuzumab (targets Erb2), Gefitinib/Iressa (targets EGFR), Ranibizumab (targets VEGF), Pegaptanib (targets VEGF), Erlotinib/Tarceva (targets Erb1), Nilotinib (targets Bcr-Abl), Lapatinib (targets Erb1 and Erb2/Her2), GW-572016/lapatinib ditosylate (targets HER2/Erb2), Panitumumab/Vectibix (targets EGFR), Vandetinib (targets RET/VEGFR), E7080 (multiple targets including RET and VEGFR), Herceptin (targets HER2/Erb2), PKI-166 (targets EGFR), Canertinib/CI-1033 (targets EGFR), Sunitinib/SU-11464/Sutent (targets EGFR and FLT3), Matuzumab/Emd7200 (targets EGFR), EKB-569 (targets EGFR), Zd6474 (targets EGFR and VEGFR), PKC-412 (targets VEGR and FLT3), Vatalanib/Ptk787/ZK222584 (targets VEGR), CEP-701 (targets FLT3), SU5614 (targets FLT3), MLN518 (targets FLT3), XL999 (targets FLT3), VX-322 (targets FLT3), Azd0530 (targets SRC), BMS-354825 (targets SRC), SKI-606 (targets SRC), CP-690 (targets JAK), AG-490 (targets JAK), WHI-P154 (targets JAK), WHI-P131 (targets JAK), sorafenib/

Nexavar (targets RAF kinase, VEGFR-1, VEGFR-2, VEGFR-3, PDGFR-B, KIT, FLT-3, and RET), Dasatinib/Sprycel (BCR/ABL and Src), AC-220 (targets Flt3), AC-480 (targets all HER proteins, "panHER"), Motesanib diphosphate (targets VEGF1-3, PDGFR, and c-kit), Denosumab (targets RANKL, inhibits SRC), AMG888 (targets HER3), and AP24534 (multiple targets including Flt3).

Exemplary serine/threonine kinase inhibitors include, but are not limited to, Rapamune (targets mTOR/FRAP1), Deforolimus (targets mTOR), Certican/Everolimus (targets mTOR/FRAP1), AP23573 (targets mTOR/FRAP1), Eril/Fasudil hydrochloride (targets RHO), Flavopiridol (targets CDK), Seliciclib/CYC202/Roscovitrine (targets CDK), SNS-032/BMS-387032 (targets CDK), Ruboxistaurin (targets PKC), Pkc412 (targets PKC), Bryostatin (targets PKC), KAI-9803 (targets PKC), SF1126 (targets PI3K), VX-680 (targets Aurora kinase), Azd1152 (targets Aurora kinase), Arry-142886/AZD-6244 (targets MAP/MEK), SCID-469 (targets MAP/MEK), GW681323 (targets MAP/MEK), CC-401 (targets JNK), CEP-1347 (targets JNK), and PD 332991 (targets CDK).

Additionally, the peptide composition described herein can be co-administered with conventional immunotherapeutic agents including, but not limited to, immunostimulants (e.g., *Bacillus* Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-*pseudomonas* exotoxin conjugate, etc.), and radioimmunotherapy (e.g., anti-CD20 monoclonal antibody conjugated to $^{111}$In, $^{90}$Y, or $^{131}$I, etc.).

In embodiments, the peptide composition described herein can be co-administered with conventional radiotherapeutic agents including, but not limited to, radionuclides such as $^{47}$Sc, $^{64}$Cu, $^{67}$Cu, $^{89}$Sr, $^{86}$Y, $^{87}$Y, $^{90}$Y, $^{105}$Rh, $^{111}$Ag, $^{111}$In, $^{117m}$Sn, $^{149}$Pm, $^{153}$Sm, $^{166}$Ho, $^{177}$Lu, $^{186}$Re, $^{188}$Re, $^{211}$At, and $^{212}$Bi, optionally conjugated to antibodies directed against tumor antigens.

In embodiments, the anti-cancer agent used herein refers to Doxorubicin, Cisplatin, Carboplatin, Taxanes, Camptothecin or any combination thereof.

As used herein, a "subject in need thereof" or "a patient" is a subject having cancer or a subject having a precancerous condition. In embodiments, a subject in need thereof has cancer. A "subject" or a "patient" includes a mammal. The mammal can be e.g., a human or appropriate non-human mammal, such as primate, mouse, rat, dog, cat, cow, horse, goat, camel, sheep or a pig. The subject can also be a bird or fowl. In embodiments, the mammal is a human. Thus the methods are applicable to both human therapy and veterinary applications.

In embodiments, a "subject in need thereof" has already undergone, is undergoing or will undergo, at least one therapeutic intervention for the cancer or precancerous condition.

A subject in need thereof may have refractory cancer on most recent therapy. "Refractory cancer" means cancer that does not respond to treatment. The cancer may be resistant at the beginning of treatment or it may become resistant during treatment. Refractory cancer is also called resistant cancer. In some embodiments, the subject in need thereof has cancer recurrence following remission on most recent therapy. In some embodiments, the subject in need thereof received and failed all known effective therapies for cancer treatment. In some embodiments, the subject in need thereof received at least one prior therapy.

As used herein, the term "cancer" refers to all types of cancer, neoplasm or malignant tumors found in mammals, including leukemias, lymphomas, melanomas, neuroendocrine tumors, carcinomas and sarcomas. Exemplary cancers that may be treated with a composition, pharmaceutical composition, or method provided herein include lymphoma, sarcoma, bladder cancer, bone cancer, brain tumor, cervical cancer, colon cancer, esophageal cancer, gastric cancer, head and neck cancer, kidney cancer, myeloma, thyroid cancer, leukemia, prostate cancer, breast cancer (e.g. triple negative, ER positive, ER negative, chemotherapy resistant, herceptin resistant, HER2 positive, doxorubicin resistant, tamoxifen resistant, ductal carcinoma, lobular carcinoma, primary, metastatic), ovarian cancer, pancreatic cancer, liver cancer (e.g., hepatocellular carcinoma), lung cancer (e.g. non-small cell lung carcinoma, squamous cell lung carcinoma, adenocarcinoma, large cell lung carcinoma, small cell lung carcinoma, carcinoid, sarcoma), glioblastoma multiforme, glioma, melanoma, prostate cancer, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma. Additional examples include, cancer of the thyroid, endocrine system, brain, breast, cervix, colon, head & neck, esophagus, liver, kidney, lung, non-small cell lung, melanoma, mesothelioma, ovary, sarcoma, stomach, uterus or Medulloblastoma, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, Paget's Disease of the Nipple, Phyllodes Tumors, Lobular Carcinoma, Ductal Carcinoma, cancer of the pancreatic stellate cells, cancer of the hepatic stellate cells, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a composition, pharmaceutical composition, or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

The term "sarcoma" generally refers to a tumor which is made up of a substance like the embryonic connective tissue and is generally composed of closely packed cells embedded in a fibrillar or homogeneous substance. Sarcomas that may be treated with a composition, pharmaceutical composition, or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a composition, pharmaceutical composition, or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

"Breast cancer" includes all forms of cancer of the breast. Breast cancer can include primary epithelial breast cancers. Breast cancer can include cancers in which the breast is involved by other tumors such as lymphoma, sarcoma or melanoma. Breast cancer can include carcinoma of the breast, ductal carcinoma of the breast, lobular carcinoma of the breast, undifferentiated carcinoma of the breast, cystosarcoma phyllodes of the breast, angiosarcoma of the breast, and primary lymphoma of the breast. Breast cancer can include Stage I, II, IIIA, IIIB, IIIC and IV breast cancer. Ductal carcinoma of the breast can include invasive carcinoma, invasive carcinoma in situ with predominant intraductal component, inflammatory breast cancer, and a ductal carcinoma of the breast with a histologic type selected from the group consisting of comedo, mucinous (colloid), medullary, medullary with lymphcytic infiltrate, papillary, scirrhous, and tubular. Lobular carcinoma of the breast can include invasive lobular carcinoma with predominant in situ component, invasive lobular carcinoma, and infiltrating lobular carcinoma. Breast cancer can include Paget's disease, Paget's disease with intraductal carcinoma, and Paget's disease with invasive ductal carcinoma. Breast cancer can include breast neoplasms having histologic and ultrastructual heterogeneity (e.g., mixed cell types).

A breast cancer that is to be treated can include familial breast cancer. A breast cancer that is to be treated can include sporadic breast cancer. A breast cancer that is to be treated can arise in a male subject. A breast cancer that is to be treated can arise in a female subject. A breast cancer that is to be treated can arise in a premenopausal female subject or a postmenopausal female subject. A breast cancer that is to be treated can arise in a subject equal to or older than 30 years old, or a subject younger than 30 years old. A breast cancer that is to be treated has arisen in a subject equal to or older than 50 years old, or a subject younger than 50 years old. A breast cancer that is to be treated can arise in a subject equal to or older than 70 years old, or a subject younger than 70 years old.

A breast cancer that is to be treated can be typed to identify a familial or spontaneous mutation in BRCA1, BRCA2, or p53. A breast cancer that is to be treated can be typed as having a HER2/neu gene amplification, as overexpressing HER2/neu, or as having a low, intermediate or high level of HER2/neu expression. A breast cancer that is to be treated can be typed for a marker selected from the group consisting of estrogen receptor (ER), progesterone receptor (PR), human epidermal growth factor receptor-2, Ki-67, CA15-3, CA 27-29, and c-Met. A breast cancer that is to be treated can be typed as ER-unknown, ER-rich or ER-poor. A breast cancer that is to be treated can be typed as ER-negative or ER-positive. ER-typing of a breast cancer may be performed by any reproducible means. ER-typing of a breast cancer may be performed as set forth in Onkologie 27: 175-179 (2004). A breast cancer that is to be treated can be typed as PR-unknown, PR-rich, or PR-poor. A breast cancer that is to be treated can be typed as PR-negative or PR-positive. A breast cancer that is to be treated can be typed as receptor positive or receptor negative. A breast cancer that is to be treated can be typed as being associated with elevated blood levels of CA 15-3, or CA 27-29, or both. A breast cancer that is to be treated can be "triple-negative breast cancer" (TNBC) (estrogen receptor [ER]-negative, progesterone receptor [PR]-negative, and human epidermal growth factor receptor 2 [HER2]-negative).

A breast cancer that is to be treated can include a localized tumor of the breast. A breast cancer that is to be treated can include a tumor of the breast that is associated with a negative sentinel lymph node (SLN) biopsy. A breast cancer that is to be treated can include a tumor of the breast that is associated with a positive sentinel lymph node (SLN) biopsy. A breast cancer that is to be treated can include a tumor of the breast that is associated with one or more positive axillary lymph nodes, where the axillary lymph nodes have been staged by any applicable method. A breast cancer that is to be treated can include a tumor of the breast that has been typed as having nodal negative status (e.g., node-negative) or nodal positive status (e.g., node-positive). A breast cancer that is to be treated can include a tumor of the breast that has metastasized to other locations in the body. A breast cancer that is to be treated can be classified as having metastasized to a location selected from the group consisting of bone, lung, liver, or brain. A breast cancer that is to be treated can be classified according to a characteristic selected from the group consisting of metastatic, localized, regional, local-regional, locally advanced, distant, multicentric, bilateral, ipsilateral, contralateral, newly diagnosed, recurrent, and inoperable.

The term "carcinoma" refers to a malignant new growth made up of epithelial cells tending to infiltrate the surrounding tissues and give rise to metastases. Exemplary carcinomas that may be treated with a composition, pharmaceutical composition, or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, ductal carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lobular carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma *mucosum*, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tubular carcinoma, tuberous carcinoma, verrucous carcinoma, or carcinoma villosum.

As used herein, the terms "metastasis," "metastatic," and "metastatic cancer" can be used interchangeably and refer to the spread of a proliferative disease or disorder, e.g., cancer, from one organ or another non-adjacent organ or body part. Cancer occurs at an originating site, e.g., breast, which site is referred to as a primary tumor, e.g., primary breast cancer. Some cancer cells in the primary tumor or originating site acquire the ability to penetrate and infiltrate surrounding normal tissue in the local area and/or the ability to penetrate the walls of the lymphatic system or vascular system circulating through the system to other sites and tissues in the body. A second clinically detectable tumor formed from cancer cells of a primary tumor is referred to as a metastatic or secondary tumor. When cancer cells metastasize, the metastatic tumor and its cells are presumed to be similar to those of the original tumor. Thus, if lung cancer metastasizes to the breast, the secondary tumor at the site of the breast consists of abnormal lung cells and not abnormal breast cells. The secondary tumor in the breast is referred to a metastatic lung cancer. Thus, the phrase metastatic cancer refers to a disease in which a subject has or had a primary tumor and has one or more secondary tumors. The phrases non-metastatic cancer or subjects with cancer that is not metastatic refers to diseases in which subjects have a primary tumor but not one or more secondary tumors. For example, metastatic lung cancer refers to a disease in a subject with or with a history of a primary lung tumor and with one or more secondary tumors at a second location or multiple locations, e.g., in the breast.

A cancer that is to be treated can be staged according to the American Joint Committee on Cancer (AJCC) TNM classification system, where the tumor (T) has been assigned a stage of TX, T1, T1mic, T1a, T1b, T1c, T2, T3, T4, T4a, T4b, T4c, or T4d; and where the regional lymph nodes (N) have been assigned a stage of NX, N0, N1, N2, N2a, N2b, N3, N3a, N3b, or N3c; and where distant metastasis (M) can be assigned a stage of MX, M0, or M1. A cancer that is to be treated can be staged according to an American Joint Committee on Cancer (AJCC) classification as Stage I, Stage IIA, Stage JIB, Stage IIIA, Stage IIIB, Stage IIIC, or Stage IV. A cancer that is to be treated can be assigned a grade according to an AJCC classification as Grade GX (e.g., grade cannot be assessed), Grade 1, Grade 2, Grade 3 or Grade 4. A cancer that is to be treated can be staged according to an AJCC pathologic classification (pN) of pNX, pN0, PN0 (I−), PN0 (I+), PN0 (mol−), PN0 (mol+), PN1, PN1(mi), PN1a, PN1b, PN1c, pN2, pN2a, pN2b, pN3, pN3a, pN3b, or pN3c.

A cancer that is to be treated can include a tumor that has been determined to be less than or equal to about 2 centimeters in diameter. A cancer that is to be treated can include a tumor that has been determined to be from about 2 to about 5 centimeters in diameter. A cancer that is to be treated can include a tumor that has been determined to be greater than or equal to about 3 centimeters in diameter. A cancer that is to be treated can include a tumor that has been determined to be greater than 5 centimeters in diameter. A cancer that is to be treated can be classified by microscopic appearance as well differentiated, moderately differentiated, poorly differentiated, or undifferentiated. A cancer that is to be treated can be classified by microscopic appearance with respect to mitosis count (e.g., amount of cell division) or nuclear pleiomorphism (e.g., change in cells). A cancer that is to be treated can be classified by microscopic appearance as being associated with areas of necrosis (e.g., areas of dying or degenerating cells). A cancer that is to be treated can be classified as having an abnormal karyotype, having an abnormal number of chromosomes, or having one or more chromosomes that are abnormal in appearance. A cancer that is to be treated can be classified as being aneuploid, triploid, tetraploid, or as having an altered ploidy. A cancer that is to be treated can be classified as having a chromosomal translocation, or a deletion or duplication of an entire chromosome, or a region of deletion, duplication or amplification of a portion of a chromosome.

A cancer that is to be treated can be evaluated by DNA cytometry, flow cytometry, or image cytometry. A cancer that is to be treated can be typed as having about 10%, 20%, 30%, 40%, 50%, 60%, 70%, 80%, or 90% of cells in the synthesis stage of cell division (e.g., in S phase of cell division). A cancer that is to be treated can be typed as having a low S-phase fraction or a high S-phase fraction.

An "effective amount" or "a therapeutically effective amount" as provided herein is an amount sufficient to accomplish a stated purpose (e.g. achieve the effect for which it is administered, treat a disease, reduce enzyme activity, increase enzyme activity, reduce transcriptional activity, increase transcriptional activity, reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist (inhibitor) required to decrease the activity of an enzyme or protein (e.g. transcription factor) relative to the absence of the antagonist. An "activity increasing amount," as used herein, refers to an amount of agonist (activator) required to increase the activity of an enzyme or protein (e.g. transcription factor) relative to the absence of the agonist. A "function disrupting amount," as used herein, refers to the amount of antagonist (inhibitor) required to disrupt the function of an enzyme or protein (e.g. transcription factor) relative to the absence of the antagonist. A "function increasing amount," as used herein, refers to the amount of agonist (activator) required to increase the function of an enzyme or protein (e.g. transcription factor) relative to the absence of the agonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy,* 20th Edition, 2003, Gennaro, Ed., Lippincott, Williams & Wilkins). In embodiments, the disease or condition to be treated is cancer.

As used herein, "treating" or "treat" describes the management and care of a patient for the purpose of combating a disease, condition, or disorder and includes the administration of a composition of the present invention to alleviate the symptoms or complications of a disease, condition or disorder, or to eliminate the disease, condition or disorder. The term "treat" can also include treatment of a cell in vitro or an animal model.

As used herein, the term "alleviate" is meant to describe a process by which the severity of a sign or symptom of a disorder is decreased. Importantly, a sign or symptom can be alleviated without being eliminated. The administration of compositions or pharmaceutical compositions of the invention may or can lead to the elimination of a sign or symptom, however, elimination is not required. Effective dosages should be expected to decrease the severity of a sign or symptom. For instance, a sign or symptom of a disorder such as cancer, which can occur in multiple locations, is alleviated if the severity of the cancer is decreased within at least one of multiple locations.

As used herein, the term "severity" is meant to describe the potential of cancer to transform from a precancerous, or benign, state into a malignant state. Alternatively, or in addition, severity is meant to describe a cancer stage, for example, according to the TNM system (accepted by the International Union Against Cancer (UICC) and the American Joint Committee on Cancer (AJCC)) or by other art-recognized methods. Cancer stage refers to the extent or severity of the cancer, based on factors such as the location of the primary tumor, tumor size, number of tumors, and lymph node involvement (spread of cancer into lymph nodes). Alternatively, or in addition, severity is meant to describe the tumor grade by art-recognized methods (see, National Cancer Institute, www.cancer.gov). Tumor grade is a system used to classify cancer cells in terms of how abnormal they look under a microscope and how quickly the tumor is likely to grow and spread. Many factors are considered when determining tumor grade, including the structure and growth pattern of the cells. The specific factors used to determine tumor grade vary with each type of cancer. Severity also describes a histologic grade, also called differentiation, which refers to how much the tumor cells resemble normal cells of the same tissue type (see, National Cancer Institute, www.cancer.gov). Furthermore, severity describes a nuclear grade, which refers to the size and shape of the nucleus in tumor cells and the percentage of tumor cells that are dividing (see, National Cancer Institute, www.cancer.gov).

Severity can also describe the degree to which a tumor has secreted growth factors, degraded the extracellular matrix, become vascularized, lost adhesion to juxtaposed tissues, or metastasized. Moreover, severity can describe the number of locations to which a primary tumor has metastasized. Finally, severity can include the difficulty of treating tumors of varying types and locations. For example, inoperable tumors, those cancers which have greater access to multiple body systems (hematological and immunological tumors), and those which are the most resistant to traditional treatments are considered most severe. In these situations, prolonging the life expectancy of the subject and/or reducing pain, decreasing the proportion of cancerous cells or restricting cells to one system, and improving cancer stage/tumor grade/histological grade/nuclear grade are considered alleviating a sign or symptom of the cancer.

As used herein the term "symptom" is defined as an indication of disease, illness, injury, or that something is not right in the body. Symptoms are felt or noticed by the individual experiencing the symptom, but may not easily be noticed by others. Others are defined as non-health-care professionals.

As used herein the term "sign" is also defined as an indication that something is not right in the body. But signs are defined as things that can be seen by a doctor, nurse, or other health care professional.

Cancer is a group of diseases that may cause almost any sign or symptom. The signs and symptoms will depend on where the cancer is, the size of the cancer, and how much it affects the nearby organs or structures. If a cancer spreads (metastasizes), then symptoms may appear in different parts of the body. For example, a cancer may also cause symptoms such as fever, fatigue, or weight loss. Pain may be an early symptom with some cancers such as bone cancers or testicular cancer. But most often pain is a symptom of advanced disease. Along with cancers of the skin, some internal cancers can cause skin signs that can be seen. These changes include the skin looking darker (hyperpigmentation), yellow (jaundice), or red (erythema); itching; or excessive hair growth.

Alternatively, or in addition, cancer subtypes present specific signs or symptoms. Changes in bowel habits or bladder function could indicate cancer. Long-term constipation, diarrhea, or a change in the size of the stool may be a sign of colon cancer. Pain with urination, blood in the urine, or a change in bladder function (such as more frequent or less frequent urination) could be related to bladder or prostate cancer.

Changes in skin condition or appearance of a new skin condition could indicate cancer. Skin cancers may bleed and look like sores that do not heal. A long-lasting sore in the mouth could be an oral cancer, especially in patients who smoke, chew tobacco, or frequently drink alcohol. Sores on the penis or vagina may either be signs of infection or an early cancer.

Unusual bleeding or discharge could indicate cancer. Unusual bleeding can happen in either early or advanced cancer. Blood in the sputum (phlegm) may be a sign of lung cancer. Blood in the stool (or a dark or black stool) could be a sign of colon or rectal cancer. Cancer of the cervix or the endometrium (lining of the uterus) can cause vaginal bleeding. Blood in the urine may be a sign of bladder or kidney cancer. A bloody discharge from the nipple may be a sign of breast cancer.

A thickening or lump in the breast or in other parts of the body could indicate the presence of a cancer. Many cancers can be felt through the skin, mostly in the breast, testicle, lymph nodes (glands), and the soft tissues of the body. A lump or thickening may be an early or late sign of cancer. Any lump or thickening could be indicative of cancer, especially if the formation is new or has grown in size.

Indigestion or trouble swallowing could indicate cancer. While these symptoms commonly have other causes, indigestion or swallowing problems may be a sign of cancer of the esophagus, stomach, or pharynx (throat).

Recent changes in a wart or mole could be indicative of cancer. Any wart, mole, or freckle that changes in color, size, or shape, or loses its definite borders indicates the potential development of cancer. For example, the skin lesion may be a melanoma.

A persistent cough or hoarseness could be indicative of cancer. A cough that does not go away may be a sign of lung cancer. Hoarseness can be a sign of cancer of the larynx (voice box) or thyroid.

While the signs and symptoms listed above are the more common ones seen with cancer, there are many others that are less common and are not listed here.

Treating cancer may result in or can result in a reduction in size of a tumor. A reduction in size of a tumor may also be referred to as "tumor regression". Preferably, after treatment, tumor size would be reduced by about 5% or greater relative to its size prior to treatment; more preferably, tumor size is reduced by about 10% or greater; more preferably, reduced by about 20% or greater; more preferably, reduced by about 30% or greater; more preferably, reduced by about 40% or greater; even more preferably, reduced by about 50% or greater; and most preferably, reduced by greater than about 75% or greater. Size of a tumor may be measured by any reproducible means of measurement. The size of a tumor may be measured as a diameter of the tumor.

Treating cancer may result in or can result in a reduction in tumor volume. Preferably, after treatment, tumor volume would be reduced by about 5% or greater relative to its size prior to treatment; more preferably, tumor volume is reduced by about 10% or greater; more preferably, reduced by about 20% or greater; more preferably, reduced by about 30% or greater; more preferably, reduced by about 40% or greater; even more preferably, reduced by about 50% or greater; and most preferably, reduced by greater than about 75% or greater. Tumor volume may be measured by any reproducible means of measurement.

Treating cancer may result in or can result in a decrease in number of tumors. Preferably, after treatment, tumor number would be reduced by about 5% or greater relative to number prior to treatment; more preferably, tumor number is reduced by about 10% or greater; more preferably, reduced by about 20% or greater; more preferably, reduced by about 30% or greater; more preferably, reduced by about 40% or greater; even more preferably, reduced by about 50% or greater; and most preferably, reduced by greater than about 75%. Number of tumors may be measured by any reproducible means of measurement. The number of tumors may be measured by counting tumors visible to the naked eye or at a specified magnification. Preferably, the specified magnification is 2×, 3×, 4×, 5×, 10×, or 50×.

Treating cancer may result in or can result in a decrease in number of metastatic lesions in other tissues or organs distant from the primary tumor site. Preferably, after treatment, the number of metastatic lesions would be reduced by about 5% or greater relative to number prior to treatment; more preferably, the number of metastatic lesions is reduced by about 10% or greater; more preferably, reduced by about 20% or greater; more preferably, reduced by about 30% or greater; more preferably, reduced by about 40% or greater; even more preferably, reduced by about 50% or greater; and most preferably, reduced by greater than about 75%. The number of metastatic lesions may be measured by any reproducible means of measurement. The number of metastatic lesions may be measured by counting metastatic lesions visible to the naked eye or at a specified magnification. Preferably, the specified magnification is 2×, 3×, 4×, 5×, 10×, or 50×.

Treating cancer may result in or can result in an increase in average survival time of a population of treated subjects in comparison to a population receiving carrier alone. Preferably, the average survival time would be increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active composition. An increase in average survival time of a population may also be measured, for example, by calculating for a population the average length of survival following completion of a first round of treatment with an active composition.

Treating cancer may result in or can result in an increase in average survival time of a population of treated subjects in comparison to a population of untreated subjects. Preferably, the average survival time would be increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active composition. An increase in average survival time of a population may also be measured, for example, by calculating for a population the average length of survival following completion of a first round of treatment with an active composition.

Treating cancer may result in or can result in increase in average survival time of a population of treated subjects in comparison to a population receiving monotherapy with a drug that is not a composition of the present invention.

Preferably, the average survival time would be increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active composition. An increase in average survival time of a population may also be measured, for example, by calculating for a population the average length of survival following completion of a first round of treatment with an active composition.

Treating cancer may result in or can result in a decrease in the mortality rate of a population of treated subjects in comparison to a population receiving carrier alone. Treating cancer may result in or can result in a decrease in the mortality rate of a population of treated subjects in comparison to an untreated population. Treating cancer may result in or can result in a decrease in the mortality rate of a population of treated subjects in comparison to a population receiving monotherapy with a drug that is not a composition of the present invention, or a pharmaceutically acceptable salt, prodrug, metabolite, analog or derivative thereof. Preferably, the mortality rate would be decreased by more than 2%; more preferably, by more than 5%; more preferably, by more than 10%; and most preferably, by more than 25%. A decrease in the mortality rate of a population of treated subjects may be measured by any reproducible means. A decrease in the mortality rate of a population may be measured, for example, by calculating for a population the average number of disease-related deaths per unit time following initiation of treatment with an active composition. A decrease in the mortality rate of a population may also be measured, for example, by calculating for a population the average number of disease-related deaths per unit time following completion of a first round of treatment with an active composition.

Treating cancer may result in or can result in a decrease in tumor growth rate. Preferably, after treatment, tumor growth rate would be reduced by at least 5% relative to number prior to treatment; more preferably, tumor growth rate would be reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Tumor growth rate may be measured by any reproducible means of measurement. Tumor growth rate can be measured according to a change in tumor diameter per unit time.

Treating cancer may result in or can result in a decrease in tumor regrowth. Preferably, after treatment, tumor regrowth would be less than 5%; more preferably, tumor regrowth would be less than 10%; more preferably, less than 20%; more preferably, less than 30%; more preferably, less than 40%; more preferably, less than 50%; even more preferably, less than 50%; and most preferably, less than 75%. Tumor regrowth may be measured by any reproducible means of measurement. Tumor regrowth is measured, for example, by measuring an increase in the diameter of a tumor after a prior tumor shrinkage that followed treatment. A decrease in tumor regrowth is indicated by failure of tumors to reoccur after treatment has stopped.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated, however, that the resulting reaction product can be produced directly from a reaction between the added reagents or from an intermediate from one or more of the added reagents which can be produced in the reaction mixture. In embodiments contacting includes, for example, allowing a ribonucleic acid as described herein to interact with a an endonuclease and an enhancer element.

A "control" sample or value refers to a sample that serves as a reference, usually a known reference, for comparison to a test sample. For example, a test sample can be taken from a test condition, e.g., in the presence of a test compound, and compared to samples from known conditions, e.g., in the absence of the test compound (negative control), or in the presence of a known compound (positive control). A control can also represent an average value gathered from a number of tests or results. One of skill in the art will recognize that controls can be designed for assessment of any number of parameters. For example, a control can be devised to compare therapeutic benefit based on pharmacological data (e.g., half-life) or therapeutic measures (e.g., comparison of side effects). One of skill in the art will understand which standard controls are most appropriate in a given situation and be able to analyze data based on comparisons to standard control values. Standard controls are also valuable for determining the significance (e.g. statistical significance) of data. For example, if values for a given parameter are widely variant in standard controls, variation in test samples will not be considered as significant.

As defined herein, the term "inhibition", "inhibit", "inhibiting" or the like means negatively affecting (e.g. decreasing) the activity or function of a biomolecule or biological system relative to the activity or function in the absence of the inhibitor. In some embodiments inhibition refers to reduction of a disease or symptoms of disease.

As defined herein, the term "activation", "activate", "activating" or the like in reference to a activator (e.g. agonist) interaction means positively affecting (e.g. increasing) the activity or function of a biomolecule or biological system relative to the activity or function in the absence of the activator.

As used herein, the term "administering" means oral administration, administration as a suppository, topical contact, intravenous, parenteral, intraperitoneal, intramuscular, intralesional, intrathecal, intracranial, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). In embodiments, administration includes direct administration to a tumor. Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies (e.g. anti-cancer agent or chemotherapeutic). The composition of the invention can be administered alone or can be co-administered to the patient. Co-administration is meant to include simultaneous or sequential administration of the compound individually or in combination (more than one compound or agent). Thus, the preparations can also be combined, when desired, with other active substances (e.g. to reduce metabolic degradation). The compositions of the present invention can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present invention can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). In another embodiment, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). The compositions of the present invention can also be delivered as nanoparticles.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated (e.g. symptoms of cancer (e.g. prostate cancer, castration-resistant prostate cancer, breast cancer, triple negative breast cancer, glioblastoma, ovarian cancer, lung cancer, squamous cell carcinoma (e.g head, neck, or esophagus), colorectal cancer, leukemia, acute myeloid leukemia, lymphoma, B cell lymphoma, or multiple myeloma)), kind of concurrent treatment, complications from the disease being treated or other health-related problems. Other therapeutic regimens or agents can be used in conjunction with the methods and compounds of Applicants' invention. Adjustment and manipulation of established dosages (e.g., frequency and duration) are well within the ability of those skilled in the art.

For compounds or compositions described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

As used herein, the term "about" means a range of values including the specified value, which a person of ordinary skill in the art would consider reasonably similar to the specified value. In embodiments, the term "about" means within a standard deviation using measurements generally acceptable in the art. In embodiments, about means a range extending to +/−10% of the specified value. In embodiments, about means the specified value.

Compositions

The invention described herein is at least partially based upon the surprising discovery that a TWIST peptide can lead to the degradation of the TWIST protein, thereby treating cancer and inhibiting metastasis.

In one aspect, there is provided a composition including a TWIST peptide or a nucleic acid encoding the TWIST peptide bound to a delivery vehicle. In embodiments, the TWIST peptide includes a WR domain of TWIST1.

In another aspect, there is provided a fusion protein including a TWIST peptide covalently attached to a cell-penetrating peptide, where the TWIST peptide includes a WR domain of TWIST1.

In embodiments, a conjugate between a TWIST peptide or a nucleic acid encoding the TWIST peptide and a second molecule (e.g., a delivery vehicle or a cell-penetrating peptide) can be direct, e.g., by covalent bond, or indirect, e.g., by non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like). In embodiments, the conjugates are formed using peptidyl linker. In embodiments, conjugates are formed using conjugate chemistry including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, Advanced Organic Chemistry, 3rd Ed., John Wiley & Sons, New York, 1985; Hermanson, Bioconjugate Techniques, Academic Press, San Diego, 1996; and Feeney et al., Modification of Proteins; Advances in Chemistry Series, Vol. 198, American Chemical Society, Washington, D.C., 1982. In embodiments, the TWIST peptide (or nucleic acid encoding the peptide) is non-covalently attached to a second molecule (e.g., a delivery vehicle or a cell-penetrating peptide) through a non-covalent chemical reaction between a component of the peptide and a component of the second molecule. In other embodiments, the TWIST peptide (or nucleic acid encoding the peptide) is covalently bound to a second molecule (e.g., a delivery vehicle or a cell-penetrating peptide) using a covalent linker, wherein the covalent linker is attached to the TWIST peptide (or nucleic acid encoding the peptide) at one end and to the second molecule at the other end. The linker attachment to the TWIST peptide (or nucleic acid encoding the peptide) or to the second molecule may be accomplished using one or more reactive moieties, e.g., bioconjugate techniques, a covalent reactive moiety, as described herein (e.g., alkyne, azide, maleimide or thiol reactive moiety).

Useful reactive moieties or functional groups (chemical reactive functional groups) used for conjugate chemistries (click chemistries) herein include, for example:

(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;

(b) hydroxyl groups which can be converted to esters, ethers, aldehydes, etc.

(c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom;

(d) dienophile groups which are capable of participating in Diels-Alder reactions such as, for example, maleimido groups;

(e) aldehyde or ketone groups such that subsequent derivatization is possible via formation of carbonyl derivatives such as, for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups, which can be converted to disulfides, reacted with acyl halides, or bonded to metals such as gold;

(h) amine or sulfhydryl groups, which can be, for example, acylated, alkylated or oxidized;

(i) alkenes, which can undergo, for example, cycloadditions, acylation, Michael addition, and the like;

(j) epoxides, which can react with, for example, amines and hydroxyl compounds;

(k) phosphoramidites and other standard functional groups useful in nucleic acid synthesis;

(l) metal silicon oxide bonding;

(m) metal bonding to reactive phosphorus groups (e.g. phosphines) to form, for example, phosphate diester bonds; and (n) sulfones, for example, vinyl sulfone.

Chemical synthesis of compositions by joining modular units using conjugate (click) chemistry may also be sued to attach the covalent linker to the polymer and/or to the ligand or recognition moiety, which is well known in the art and described, for example, in H. C. Kolb, M. G. Finn and K. B. Sharpless ((2001). "Click Chemistry: Diverse Chemical Function from a Few Good Reactions". Angewandte Chemie International Edition 40 (11): 2004-2021); R. A. Evans ((2007). "The Rise of Azide-Alkyne 1,3-Dipolar 'Click' Cycloaddition and its Application to Polymer Science and Surface Modification". Australian Journal of Chemistry 60 (6): 384-395; W. C. Guida et al. Med. Res. Rev. p 3 1996; Spiteri, Christian and Moses, John E. ((2010). "Copper-Catalyzed Azide-Alkyne Cycloaddition: Regioselective Synthesis of 1,4,5-Trisubstituted 1,2,3-Triazoles". Angewandte Chemie International Edition 49 (1): 31-33); Hoyle, Charles E. and Bowman, Christopher N. ((2010). "Thiol-Ene Click Chemistry". Angewandte Chemie International Edition 49 (9): 1540-1573); Blackman, Melissa L. and Royzen, Maksim and Fox, Joseph M. ((2008). "Tetrazine Ligation: Fast Bioconjugation Based on Inverse-Electron-Demand Diels-Alder Reactivity". Journal of the American Chemical Society 130 (41): 13518-13519); Devaraj, Neal K. and Weissleder, Ralph and Hilderbrand, Scott A. ((2008). "Tetrazine Based Cycloadditions: Application to Pretargeted Live Cell Labeling". Bioconjugate Chemistry 19 (12): 2297-2299); Stöckmann, Henning; Neves, Andre; Stairs, Shaun; Brindle, Kevin; Leeper, Finian ((2011). "Exploring isonitrile-based click chemistry for ligation with biomolecules". Organic & Biomolecular Chemistry), all of which are hereby incorporated by reference in their entirety and for all purposes.

The reactive functional groups can be chosen such that they do not participate in, or interfere with, the chemical stability of the proteins described herein. By way of example, the TWIST peptide (or nucleic acid encoding the peptide) or the second molecule can include a vinyl sulfone or other reactive moiety (e.g., maleimide). Optionally, the TWIST peptide (or nucleic acid encoding the peptide) or the second molecule can include a reactive moiety having the formula S—S—R. R can be, for example, a protecting group. Optionally, R is hexanol. As used herein, the term hexanol includes compounds with the formula $C_6H_{13}OH$ and includes, 1-hexanol, 2-hexanol, 3-hexanol, 2-methyl-1-pentanol, 3-methyl-1-pentanol, 4-methyl-1-pentanol, 2-methyl-2-pentanol, 3-methyl-2-pentanol, 4-methyl-2-pentanol, 2-methyl-3-pentanol, 3-methyl-3-pentanol, 2,2-dimethyl-1-butanol, 2,3-dimethyl-1-butanol, 3,3-dimethyl-1-butanol, 2,3-dimethyl-2-butanol, 3,3-dimethyl-2-butanol, and 2-ethyl-1-butanol. Optionally, R is 1-hexanol.

In another aspect, there is provided a nucleic acid sequence encoding a fusion protein as disclosed herein. In embodiments, the nucleic acid sequence is part of a vector sequence.

TWIST1 and TWIST2 are basic helix-loop-helix (bHLH) transcription factors. TWIST1 and TWIST2 sequences are publicly available. For example, nucleotide sequence of TWIST1 can be found at NM_000474.3: and amino acid sequence of TWIST1 can be found at: NP_000465.1. For example, amino acid sequences of TWIST2 can be found at NP_001258822.1; and nucleotide sequence sequences of TWIST2 can be found at NM_001271893.3. Human TWIST1 protein is 202 amino acids in length, with the N-terminal half of the protein being largely disordered. As shown in FIG. 1B, the C-terminal half consists of the basic DNA binding domain (labeled as "B"), helix-loop-helix dimerization domain (labeled as "HLH"), and the TWIST box or WR domain (labeled as "WR"), which has been shown to be a transactivation domain. The WR domain is especially well conserved throughout evolution, with 100% identity between human, mouse, and frog (FIG. 1C).

One exemplary amino acid sequence of TWIST1 is provided below:

(SEQ ID NO: 12)

```
  1  mmqdvssspv spaddslsns eeepdrqqpp sgkrggrkrr ssrrsaggga gpggaagggv

 61  gggdepgspa qgkrgkksag cgggggaggg ggsssgggsp qsyeelqtqr vmanvrerqr

121  tqslneafaa lrkiiptlps dklskiqtlk laaryidfly qvlqsdelds kmascsyvah

181  erlsyafsvw rmegawsmsa sh
```

One exemplary nucleic acid sequence of TWIST1 is provided below:

(SEQ ID NO: 13)

```
   1 gaggtataag agcctccaag tctgcagctc tcgcccaact cccagacacc tcgcgggctc

  61 tgcagcaccg gcaccgtttc caggaggcct ggcggggtgt gcgtccagcc gttgggcgct

 121 ttctttttgg acctcggggc catccacacc gtcccctccc cctcccgcct ccctccccgc

 181 ctcccccgcg cgccctcccc gcggaggtcc ctcccgtccg tcctcctgct ctctcctccg

 241 cgggccgcat cgcccgggcc ggcgccgcgc gcgggggaag ctggcgggct gaggcgcccc

 301 gctcttctcc tctgccccgg gcccgcgagg ccacgcgtcg ccgctcgaga gatgatgcag

 361 gacgtgtcca gctcgccagt ctcgccggcc gacgacagcc tgagcaacag cgaggaagag

 421 ccagaccggc agcagccgcc gagcggcaag cgcgggggac gcaagcggcg cagcagcagg

 481 cgcagcgcgg gcggcggcgc ggggcccggc ggagccgcgg gtgggggcgt cggaggcggc

 541 gacgagccgg gcagcccggc ccagggcaag cgcggcaaga agtctgcggg ctgtggcggc

 601 ggcggcggcg cgggcggcgg cggcggcagc agcagcggcg gcgggagtcc gcagtcttac

 661 gaggagctgc agacgcagcg ggtcatggcc aacgtgcggg agcgccagcg cacccagtcg

 721 ctgaacgagg cgttcgccgc gctgcggaag atcatcccca cgctgccctc ggacaagctg

 781 agcaagattc agaccctcaa gctggcggcc aggtacatcg acttcctcta ccaggtcctc

 841 cagagcgacg agctggactc caagatggca agctgcagct atgtggctca cgagcggctc

 901 agctacgcct tctcggtctg gaggatggag ggggcctggt ccatgtccgc gtcccactag

 961 caggcggagc cccccacccc ctcagcaggg ccggagacct agatgtcatt gtttccagag

1021 aaggagaaaa tggacagtct agagactctg gagctggata actaaaaata aaaatatatg

1081 ccaaagattt tcttggaaat tagaagagca aaatccaaat tcaaagaaac agggcgtggg

1141 gcgcactttt aaaagagaaa gcgagacagg cccgtggaca gtgattccca gacgggcagc

1201 ggcaccatcc tcacacctct gcattctgat agaagtctga acagttgttt gtgttttttt

1261 tttttttttt tttgacgaag aatgttttta tttttatttt tttcatgcat gcattctcaa

1321 gaggtcgtgc caatcagcca ctgaaaggaa aggcatcact atggactttc tctattttaa

1381 aatggtaaca atcagaggaa ctataagaac acctttagaa ataaaaatac tgggatcaaa

1441 ctggcctgca aaaccatagt cagttaattc tttttttcat ccttcctctg aggggaaaaa

1501 caaaaaaaaa cttaaaatac aaaaaacaac attctattta tttattgagg acccatggta

1561 aaatgcaaat agatccggtg tctaaatgca ttcatatttt tatgattgtt ttgtaaatat

1621 ctttgtatat ttttctgcaa taaataaata taaaaaattt agagaaaaa
```

One exemplary amino acid sequence of TWIST2 is provided below:

```
                                              (SEQ ID NO: 14)
  1  meegssspvs pvdslgtsee elerqpkrfg rkrryskkss edgsptpgkr gkkgspsaqs

 61  feelqsqril anvrerqrtq slneafaalr kiiptlpsdk lskiqtlkla aryidflyqv

121  lqsdemdnkm tscsyvaher lsyafsvwrm egawsmsash
```

One exemplary nucleic acid sequence of TWIST2 is provided below:

```
                                              (SEQ ID NO: 15)
   1 ctagagtttc caaaaaagtt agaataactt cctctcccgg agacctcggt tttgcacaag

  61 ccggccttga aatcagagcc tttccagcaa ctccgagagc gtgtgctcgg cgaccgcggg

 121 cttggccagc ggcgcgcgct cggcgccccg gcgcccccag ccccacgcgc gccgggcggg

 181 cgccatggag gagggctcca gctcgcccgt gtcccccgtg gacagcctgg gcaccagcga

 241 ggaggagctc gagaggcagc ccaagcgctt cggccggaag cggcgctaca gcaagaagtc

 301 gagcgaagat ggcagcccga ccccgggcaa gcgcggcaag aagggcagcc ccagcgcgca

 361 gtccttcgag gagctgcaga gccagcgcat cctggccaac gtgcgcgagc gccagcgcac

 421 ccagtcgctc aacgaggcct tcgcggcgct gcgcaagatc atccccacgc tgccctctga

 481 caagctgagc aagatccaga cgctcaagct ggccgccagg tacatagact tcctctacca

 541 ggtcctgcag agcgacgaga tggacaataa gatgaccagc tgcagctacg tggcccacga

 601 gcgcctcagc tacgccttct ccgtgtggcg catggagggc gcgtggtcca tgtccgcctc

 661 ccactagcgc cgcgccaccc acctccggac cggcgcgcca gggctgtccg tcgcgtcggc

 721 ggcgcaagtg gaattgggat gcattcgagt ctgtaacttc tgaaacctga acaacctcag

 781 gaggccccca cctctgccct ccaccagcgt cgagagaagg gacagcagtg acatcggaca

 841 gaagacccgg gctcccgtcc tcccccagga cggtccccac ataggaaggg cactcccagc

 901 cctcttgctg gtgacattgt catggtcatc ttgtttctgt ttggattttt cttctgggtc

961  ttatgtttgg ggggaggttt attctttctg aaaatgtcta gattcaggaa cacatttatg

1021 aggatttgga ttttgaattt gtatttccct ctaagtgcct tttttaatgt ctattttttt

1081 aataaaacag aaatgcattc ttgtacaatt ctgttgaaac tggaccaagg ctctcagaag

1141 aggacccccg agttccttcc cctcccccga gcctctgcat gattgtttca agtcagcctg

1201 gaattcttac tttcacgccg ctattctttt cctttctccg tgattgcttg gctagccatt

1261 taaaaaaaaa tattctctgt tcagtgtata tgttgcttgt ttgttttatt tattgagata

1321 tttttacaag ctaagtgact gcagtgtggc tgtgtatcct gctccccacc caggaaaaat

1381 aaagacgtcc gcgcagccat ggtctcccc
```

One skilled in the art will appreciate that TWIST (including TWIST1 and TWIST2) nucleic acid and protein molecules can vary from those publicly available, such as polymorphisms resulting in one or more substitutions, deletions, insertions, or combinations thereof, while still retaining TWIST biological activity. Accordingly, in various embodiments, the amino acid sequence of the TWIST may be about 95%, about 96%, about 97%, about 98%, about 99% identical to the TWIST1 or TWIST2 sequence publicly available, or fragment thereof. A fragment can be between 3-10 amino acids, 10-20 amino acids, 20-40 amino acids, 40-56 amino acids in length or even longer. Amino acid sequences having about 95%, about 96%, about 97%, about 98%, about 99% identity to the fragments described herein are also included within the scope of the present invention.

In embodiments, the nucleic acid sequence of the TWIST may be about 95%, about 96%, about 97%, about 98%, about 99% identical to the TWIST1 or TWIST2 sequence publicly available, or fragment thereof. A fragment can be between 3-10 nucleotides, 10-20 nucleotides, 20-40 nucleotides, 40-56 nucleotides in length or even longer. Nucleic acid sequences having about 95%, about 96%, about 97%, about 98%, about 99% identity to the fragments described herein are also included within the scope of the present invention.

A "TWIST peptide" as used herein refers to a polypeptide that is derived from a TWIST1 protein or a TWIST2 protein.

In embodiments, a TWIST peptide is about at least 10 amino acids (e.g., at least 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 amino acids) in length. In embodiments, a TWIST peptide includes a WR domain of TWIST1. In embodiments, the TWIST peptide is derived from a WR domain of TWIST1. In embodiments, a TWIST peptide includes an amino acid sequence of LSYAFSVWRMEGAWSMSASH (SEQ ID NO:1). In embodiments, a TWIST peptide includes an amino acid sequence having at least 50%, 80%, 90%, 95%, 96%, 97%, 98%, 99% or 100% sequence identity to SEQ ID NO: 1. In embodiments, a TWIST peptide includes an amino acid sequence of LSYAFSVWRMEGAWSMSTSH (SEQ ID NO:2). In embodiments, a TWIST peptide includes an amino acid sequence having at least 50%, 80%, 90%, 95%, 96%, 97%, 98%, 99% or 100% sequence identity to SEQ ID NO:2. In embodiments, a TWIST peptide includes an amino acid sequence of LSYLFGVWRMEGDAQHQKA (SEQ ID NO:3). In embodiments, a TWIST peptide includes an amino acid sequence having at least 50%, 80%, 90%, 95%, 96%, 97%, 98%, 99% or 100% sequence identity to SEQ ID NO:3.

In embodiments, the delivery vehicle is a nanoparticle. In embodiments, the delivery vehicle is a lipid vehicle. The term "delivery vehicle" or "carrier" refers to any support structure that brings about the transfer of a component of genetic material or a protein. Genetic material includes but is not limited to DNA, RNA or fragments thereof and proteins or polypeptides comprise amino acids and include but are not limited to antigens, antibodies, ligands, receptors or fragments thereof. Delivery vehicles include but are not limited to vectors such as viruses (examples include but are not limited to retroviruses, adenoviruses, adeno-associated viruses, pseudotyped viruses, replication competent viruses, herpes simplex virus), virus capsids, liposomes or liposomal vesicles, lipoplexes, polyplexes, dendrimers, macrophages, artificial chromosomes, nanoparticles, polymers and also hybrid particles, examples of which include virosomes. Delivery vehicles may have multiple surfaces and compartments for attachment and storage of components. These include but are not limited to outer surfaces and inner compartments.

In embodiments, the delivery vehicle is a nanoparticle or a lipid particle or a viral vector. Any nanoparticles known for protein or nucleic acid delivery can be used for the invention described herein. Nanoparticles are particles between 1 and 100 nanometers in size. Recent dramatic advances in nanotechnology have led to the development of a variety of nanoparticles (NPs) that provide valuable tools. Numerous nanomaterials such as polymers, liposomes, protein based NPs and inorganic NPs have been developed and a variety of particles are currently being evaluated in clinical studies with promising initial results; and some liposomal NPs are approved by the FDA. One of the major advantages of using these NPs is that they offer targeted tissue/site delivery. Their small size allows NPs to escape through blood vessels at the target site through the leaky vascular structure (Enhanced permeability and retention effect). In addition to this passive mechanism, a variety of targeting moieties can be attached to NPs to confer active targeting capability. Exemplary nanoparticles that can be used for delivering compositions described herein include, but are not limited to, solid nanoparticles (e.g., metals such as silver, gold, iron, titanium), non-metal, lipid-based solids (e.g., liposome), polymers (e.g., polyethylenimene, dendrimer), suspensions of nanoparticles, or combinations thereof (e.g., polyethylenimene-liposome, dendrisome). Any compositions described herein (such as Mito-Cas9, mito-Cpf1, or other mito-RNA guided nucleases (mito-RGN)) may be delivered in nanoparticle complexes in the form of protein, DNA, or mRNA. Additional information about nanoparticles that can be used by the compositions described herein can be found in Coelho et al., N Engl J Med 2013; 369:819-29, Tabernero et al., Cancer Discovery, April 2013, Vol. 3, No. 4, pages 363-470, Zhang et al., WO2015089419 A2, and Zuris J A et al., Nat Biotechnol. 2015; 33(1):73-80, each of which is incorporated herein by reference.

In embodiments, the vector is a replication-incompetent viral vector. For example, the replication-incompetent viral vector is a replication-incompetent DNA viral vector (including, but is not limited to, adenoviruses, adeno-associated viruses). For example, the replication-incompetent viral vector is a replication-incompetent RNA viral vector (including, but is not limited to, replication defective retroviruses, lentiviruses, and rabies viruses).

In embodiments, the delivery vehicle is a lipid particle-a particle having lipid as a component, such as liposomes or liposomal vesicles or lipoplexes. Liposomes, also known as vesicles, are generally composed of phospholipids and other lipid components such as cholesterol. They can function as carriers whose essential structural feature is a bipolar lipid membrane which envelops an aqueous core volume in which pharmacological agents are solubilized and therefore encapsulated. Various lipid formulations and methods for their preparation have been described for the delivery of pharmaceutically active agents to a host. For example, Geho and Lau in U.S. Pat. No. 4,603,044 describe a targeted liposomal delivery system for delivery of a drug to the hepatobiliary receptors of the liver. The system is composed of a drug or diagnostic agent encapsulated in or associated with lipid membrane structures in the form of vesicles or liposomes, and a molecule having a fatty substituent attached to the vesicle wall and a target substituent which is a biliary attracted chemical, such as a substituted iminodiacetate complex. The system is particularly useful for the delivery of insulin and serotonin in the treatment of Types I and II diabetes, respectively. Several cationic lipid reagents have become commercially available for transfecting eukaryotic cells. These examples include Lipofectin® (DOTMA:DOPE) (Invitrogen, Carlsbad, Calif.), LipofectAmine™ (DOSPA:DOPE)(Invitrogen), LipofectAmine2000™ (Invitrogen), LipofectAmine 3000™ (Invitrogen), Lipofectamine RNAiMax™ (Invitrogen), Lipofectamme LTX™ (Thermo Fisher Scientific), Eugene®, Transfectam® (DOGS), Effectene®, DC-Chol. US Patent Publication No. 20050019923 involves cationic dendrimers for delivering bioactive molecules, such as polynucleotide molecules, peptides and polypeptides and/or pharmaceutical agents, to a mammalian body, given the low toxicity and targeting specificity. Other derivatives of cationic dendrimer mentioned in Bioactive Polymers, US published application 20080267903, may also be suitable delivery vehicles for mitoCas9 gene therapy.

Various polymeric formulations of biologically active agents and methods for their preparation have been described. U.S. Pat. Nos. 3,773,919, 3,991,776, 4,076,779, 4,093,709, 4,118,470, 4,131,648, 4,138,344, 4,293,539 and 4,675,189, inter alia, disclose the preparation and use of biocompatible, biodegradable polymers, such as poly (lactic acid), poly(glycolic acid), copolymers of glycolic and lactic acids, poly (o-hydroxycarboxy lie acid), polylactones, polyacetals, polyorthoesters and polyorthocarbonates, for the encapsulation of drugs and medicaments. These polymers mechanically entrap the active constituents and later provide controlled release of the active ingredient via polymer dissolution or degradation. Certain condensation polymers formed from divinyl ethers and polyols are described in Polymer Letters, 18, 293 (1980). Polymers have proven to be successful controlled-release drug delivery devices.

More information about liposomal constructs or polymeric constructs that can be used for the present invention can be found at Schwendener R A et al., Ther Adv Vaccines. 2014 November; 2(6): 159-182; Li Y et al., J Gene 2011, Med 13: 60-72; Pichon C et al., Methods Mol Biol 2013 969: 247-274; McNamara M A et al., J Immunol Res. 2015; 2015: 794528; Sayour E. J. et al., Journal for Immunotherapy of Cancer. 2015; 3, article 13; Bettinger T. et al, Current Opinion in Molecular Therapeutics. 2001; 3(2):116-124; Lu D. et al., Cancer Gene Therapy. 1994; 1(4):245-252; Wasungu L. et al., Journal of Controlled Release. 2006; 116(2):255-264; Little S. et al., Proceedings of the National Academy of Sciences of the United States of America. 2004; 101(26):9534-9539; Phua K. et al., Journal of Controlled Release. 2013; 166(3):227-233; Su X et al., Molecular Pharmaceutics. 2011; 8(3):774-787; Phua K. K. L. et al., Nanoscale. 2014; 6(14):7715-7729; Phua K. K. L. et al., Scientific Reports. 2014; 4, article 5128.

In embodiments, the protein is encapsulated within said delivery vehicle. Encapsulation can be carried out by any methods known in the art.

Cell-penetrating peptides (CPPs) are short peptides that facilitate cellular intake/uptake of various molecular cargo compositions (e.g., polypeptides, nano-size particles, small chemical molecules and large fragments of DNA). The "cargo" is associated with the peptides either through chemical linkage via covalent bonds or through non-covalent interactions. The function of the CPPs are to deliver the cargo into cells, a process that commonly occurs through endocytosis with the cargo delivered to delivery vectors for use in research and medicine. In embodiments, CPPs have an amino acid composition that either contains a high relative abundance of positively charged amino acids such as lysine or arginine or has sequences that contain an alternating pattern of polar/charged amino acids and non-polar, hydrophobic amino acids. These two types of structures are referred to as polycationic or amphipathic, respectively. A third class of CPPs are the hydrophobic peptides, containing only apolar residues, with low net charge or have hydrophobic amino acid groups that are crucial for cellular uptake.

In embodiments, a CPP includes an amino acid sequence of RRRRRRRRR (SEQ ID NO: 4). In embodiments, a CPP includes an amino acid sequence of RRRRRRR (SEQ ID NO:5). In embodiments, a CPP includes an amino acid sequence of RRRRRRRR (SEQ ID NO:16). In embodiments, a CPP includes an amino acid sequence of RRRRRRRRRR (SEQ ID NO:17). In embodiments, a CPP includes an amino acid sequence of RRRRRRRRRRR (SEQ ID NO:18). In embodiments, a CPP includes an amino acid sequence of RRRRRRRRRRRR (SEQ ID NO:19). In embodiments, a CPP includes an amino acid sequence of RRRRRRRRRRRRR (SEQ ID NO:20). In embodiments, a CPP includes an amino acid sequence of RRRRRRRRRRRRRR (SEQ ID NO:21). In embodiments, a CPP includes an amino acid sequence of RRRRRRRRRRRRRRR (SEQ ID NO:22) In embodiments, a CPP includes an amino acid sequence of RRRRRRRRRRRRRRRR (SEQ ID NO:23). In embodiments, a CPP includes an amino acid sequence of any one of SEQ ID NOs: 4, 5, and 16-23. In embodiments, a CPP includes an amino acid sequence having at least 50%, 80%, 90%, 95%, 96%, 97%, 98%, 99% or 100% sequence identity to SEQ ID NO:4. In embodiments, a CPP includes an amino acid sequence having at least 50%, 80%, 90%, 95%, 96%, 97%, 98%, 99% or 100% sequence identity to SEQ ID NO:5. In embodiments, a CPP includes an amino acid sequence having at least 50%, 80%, 90%, 95%, 96%, 97%, 98%, 99% or 100% sequence identity to SEQ ID NO:16. In embodiments, a CPP includes an amino acid sequence having at least 50%, 80%, 90%, 95%, 96%, 97%, 98%, 99% or 100% sequence identity to SEQ ID NO:17. In embodiments, a CPP includes an amino acid sequence having at least 50%, 80%, 90%, 95%, 96%, 97%, 98%, 99% or 100% sequence identity to SEQ ID NO:18. In embodiments, a CPP includes an amino acid sequence having at least 50%, 80%, 90%, 95%, 96%, 97%, 98%, 99% or 100% sequence identity to SEQ ID NO:19. In embodiments, a CPP includes an amino acid sequence having at least 50%, 80%, 90%, 95%, 96%, 97%, 98%, 99% or 100% sequence identity to SEQ ID NO:20. In embodiments, a CPP includes an amino acid sequence having at least 50%, 80%, 90%, 95%, 96%, 97%, 98%, 99% or 100% sequence identity to SEQ ID NO:21. In embodiments, a CPP includes an amino acid sequence having at least 50%, 80%, 90%, 95%, 96%, 97%, 98%, 99% or 100% sequence identity to SEQ ID NO:22. In embodiments, a CPP includes an amino acid sequence having at least 50%, 80%, 90%, 95%, 96%, 97%, 98%, 99% or 100% sequence identity to SEQ ID NO:23.

In embodiments, a CPP includes an amino acid sequence of GRKKRRQRRRPPQ (SEQ ID NO: 6). In embodiments, a CPP includes an amino acid sequence of RQIKIWFQNRRMKWKK (SEQ ID NO: 7). In embodiments, a CPP includes an amino acid sequence of RRRRNRTRRNRRRVR (SEQ ID NO: 8). In embodiments, a CPP includes an amino acid sequence of LLIILRRRIRKQAHAHSK (SEQ ID NO: 9). In embodiments, a CPP includes an amino acid sequence of GWTLNSAGYLLGKINLKALAALAKKIL (SEQ ID NO: 10). In embodiments, a CPP includes an amino acid sequence of MVTVLFRRLRIRRACGPPRVRV (SEQ ID NO: 11). In embodiments, a CPP includes an amino acid sequence of any one of SEQ ID NOs: 6-11. In embodiments, a CPP includes an amino acid sequence having at least 50%, 80%, 90%, 95%, 96%, 97%, 98%, 99% or 100% sequence identity to any one of SEQ ID NO:6. In embodiments, a CPP includes an amino acid sequence having at least 50%, 80%, 90%, 95%, 96%, 97%, 98%, 99% or 100% sequence identity to SEQ ID NO:7. In embodiments, a CPP includes an amino acid sequence having at least 50%, 80%, 90%, 95%, 96%, 97%, 98%, 99% or 100% sequence identity to SEQ ID NO:8. In embodiments, a CPP includes an amino acid sequence having at least 50%, 80%, 90%, 95%, 96%, 97%, 98%, 99% or 100% sequence identity to SEQ ID NO:9. In embodiments, a CPP includes an amino acid sequence having at least 50%, 80%, 90%, 95%, 96%, 97%, 98%, 99% or 100% sequence identity to SEQ ID NO:10. In embodiments, a CPP includes an amino acid sequence having at least 50%, 80%, 90%, 95%, 96%, 97%, 98%, 99% or 100% sequence identity to SEQ ID NO:11.

Methods

The invention further provides methods of using the compositions described herein. In another aspect, there is provided a method of treating cancer in a subject in need thereof. The method includes administering to the subject a therapeutically effective amount of a TWIST inhibitor described herein.

In another aspect, there is provided a method of inhibiting metastasis in a subject in need thereof. The method includes administering to the subject a therapeutically effective amount of a TWIST inhibitor described herein.

In some embodiments, a TWIST inhibitor is an inhibitor for both TWIST1 and TWIST2. In some embodiments, a TWIST inhibitor is a TWIST peptide. In some embodiments, a TWIST inhibitor is a composition (e.g., a TWIST peptide bound to a delivery vehicle or a fusion protein including a TWIST peptide) described herein. In some embodiments, a TWIST inhibitor is a pharmaceutical composition described herein.

Further to any method above and embodiment thereof, in embodiments, the subject is resistant to an anti-cancer drug.

Further to any method above and embodiment thereof, in embodiments the method further includes administering to the subject a therapeutically effective amount of an anti-cancer agent.

Further to any method above and embodiment thereof, in embodiments the anti-cancer agent is doxorubicin, cisplatin, carboplatin, a taxane, camptothecin or any combination thereof.

Further to any method above and embodiment thereof, in embodiments the TWIST inhibitor is within a pharmaceutical composition including the TWIST inhibitor and a pharmaceutically acceptable excipient.

Further to any method above and embodiment thereof, in embodiments the therapeutically effective amount of the TWIST inhibitor is an amount sufficient to re-sensitize the subject to subsequent treatment with an anti-cancer agent.

The terms effective amount and effective dosage are used interchangeably. The term effective amount is defined as any amount necessary to produce a desired physiologic response. In this case, for example, a desired physiologic response includes a subject being more (e.g., about 5%, 10%, 15%, 20%, 25%, 30%, 35%, 40%, 45%, 50%, 75%, 100% or more) responsive when administered with a TWIST inhibitor compared to the response level of the subject without taking the TWIST inhibitor. A skilled artisan would readily determine the signs of being responsive (such as, slower progression of cancer, smaller size of the cancer tissue, etc.). Effective amounts and schedules for administering the agent may be determined empirically, and making such determinations is within the skill in the art. The dosage ranges for administration are those large enough to produce the desired effect in which one or more symptoms of the disease or disorder are affected (e.g., reduced or delayed). The dosage should not be so large as to cause substantial adverse side effects, such as unwanted cross-reactions, anaphylactic reactions, and the like. Generally, the dosage will vary with the age, condition, sex, type of disease, the extent of the disease or disorder, route of administration, or whether other drugs are included in the regimen, and can be determined by one of skill in the art. The dosage can be adjusted by the individual physician in the event of any contraindications. Dosages can vary, and can be administered in one or more dose administrations daily, for one or several days. Guidance can be found in the literature for appropriate dosages for given classes of pharmaceutical products.

In some embodiments, the TWIST inhibitor and the anti-cancer agent are administered in a single composition, e.g., as being bound to the same delivery vehicle. In some embodiment, the TWIST inhibitor and the anti-cancer agent are released simultaneously. In some embodiment, the anti-cancer agent is released after the TWIST inhibitor takes effect. For example, the anti-cancer agent is released one or more hours, or one or more days after the TWIST inhibitor takes effect. For example, the anti-cancer drug is released about 30 min, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days or more after the TWIST inhibitor takes effect.

In some embodiments, the TWIST inhibitor and the anti-cancer agent are administered in two or more compositions, as being bound to different delivery vehicles.

In some embodiment, the compositions containing TWIST inhibitor and the anti-cancer agent are administered simultaneously. Optionally, the anti-cancer agent is released simultaneously as the TWIST inhibitor takes effect. Optionally, the anti-cancer agent is released about 30 min, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days or more after the TWIST inhibitor takes effect.

In some embodiments, the composition(s) containing the anti-cancer agent is administered after the administration of the composition containing the TWIST inhibitor. For example, the composition(s) containing the anti-cancer agent is administered and released about 30 min, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days or more after the TWIST inhibitor is administered and takes effect.

The TWIST inhibitor takes effect when the expression level of TWIST gene or TWIST protein or the activity level of TWIST protein is less than 90% of the initial level, less than 80% of the initial level, less than 70% of the initial level, less than 60% of the initial level, less than 50% of the initial level, less than 40% of the initial level, less than 30% of the initial level, less than 20% of the initial level or less than 10% of the initial level. Methods for determining the expression level of TWIST gene or TWIST protein or the activity level of TWIST protein is well known in the art.

EMBODIMENTS

Embodiment 1

A method of treating cancer in a subject in need thereof, the method comprising administering to the subject a therapeutically effective amount of a TWIST inhibitor, wherein the TWIST inhibitor comprises a TWIST peptide.

Embodiment 2

A method of inhibiting metastasis in a subject in need thereof, the method comprising administering to the subject a therapeutically effective amount of a TWIST inhibitor, wherein the TWIST inhibitor comprises a TWIST peptide.

Embodiment 3

The method of Embodiment 1 or 2, wherein the TWIST1 peptide comprises an amino acid sequence of SEQ ID NO: 1.

Embodiment 4

The method of Embodiment 1 or 2, wherein the TWIST1 peptide is bound to a delivery vehicle.

Embodiment 5

The method of Embodiment 4, wherein the delivery vehicle is a nanoparticle or a lipid vehicle.

Embodiment 6

The method of any one of Embodiments 1 to 5, wherein the TWIST1 peptide is covalently linked to a cell-penetrating peptide.

Embodiment 7

The method of Embodiment 6, wherein the cell-penetrating peptide comprises an amino acid sequence of SEQ ID NO:4.

Embodiment 8

The method of Embodiment 1 or 2, wherein the subject is resistant to an anti-cancer drug.

Embodiment 9

The method of Embodiment 1 or 2, further comprising administering to the subject a therapeutically effective amount of an anti-cancer agent.

Embodiment 10

The method of Embodiment 8 or 9, wherein the anti-cancer agent is doxorubicin, cisplatin, carboplatin, a taxane, camptothecin, or a combination of two or more thereof.

Embodiment 11

The method of any one of Embodiments 1 to 10, wherein the TWIST inhibitor is within a pharmaceutical composition comprising the TWIST inhibitor and a pharmaceutically acceptable excipient.

Embodiment 12

The method of Embodiment 1 or 2, wherein the therapeutically effective amount is an amount sufficient to re-sensitize the subject to subsequent treatment with an anti-cancer agent.

Embodiment 13

A composition comprising a TWIST peptide or a nucleic acid encoding the TWIST peptide bound to a delivery vehicle, wherein the TWIST peptide comprises a WR domain of TWIST1.

Embodiment 14

A fusion protein comprising a TWIST peptide covalently attached to a cell-penetrating peptide, wherein the TWIST peptide comprises a WR domain of TWIST1.

Embodiment 15

A nucleic acid sequence encoding the fusion protein of Embodiment 14.

Embodiment 16

The nucleic acid sequence of Embodiment 15, wherein the nucleic acid sequence is part of a vector sequence.

EXAMPLES

Example 1. Disruption of TWIST1-RELA Binding by Mutation and Competitive Inhibition to Validate the TWIST1 WR Domain as a Therapeutic Target Given its importance in mediating not only protein-protein interactions, but also the DNA binding activity of TWIST1, the inventors hypothesized that the WR domain was a potential target to block a TWIST1 functions associated with cancer. To test this hypothesis, the inventors sought specific residues mediating the interaction with RELA using their model system [14], and further demonstrated that a WR domain mimetic can abrogate TWIST1 activity in vitro, providing further evidence that blocking this interaction will be an effective cancer therapeutic.

In this study, the inventors identified well-conserved residues within the WR domain and used alanine scanning to determine their contribution to WR domain-mediated protein binding. Co-immunoprecipitation was used to assay binding affinity between TWIST1 and the NFκB subunit p65 (RELA). Biological activity of this complex was assayed using a dual luciferase assay system in which firefly luciferase was driven by the interleukin-8 promoter, which responds to the TWIST1-RELA complex. Finally, in order to inhibit the TWIST1-RELA interaction, the inventors created a fusion protein comprising GFP and the WR domain. Cell fractionation and proteasome inhibition experiments were utilized to elucidate the mechanism of action of the GFP-WR fusion.

The inventors found that the central residues of the WR domain (W190, R191, E193) was important for TWIST1 binding to RELA, and for upregulation of the pro-invasive cytokine interleukin 8. The inventors also found that the C-terminal 245 residues of RELA was involved in this interaction. Finally, the inventors found the GFP-WR fusion protein antagonized TWIST1-RELA binding and downstream signaling. Accordingly, the data provides evidence that occlusion of the WR domain is a therapeutic modality.

Methods.

HEK-293 cells were grown in McCoy's 5A medium supplemented with 10% fetal bovine serum (FBS) and 1% penicillin/streptomycin (P/S). Ovcar4 cells were grown in RPMI medium with 10% FBS and 1% P/S. All cells were maintained at 37° C. and 90% humidity in a tissue culture incubator with 5% $CO_2$ atmosphere. Cells were passaged every 2-4 days as they became confluent, using 0.25% trypsin. Where indicated, cells were transfected using 5 μL per well Lipofectamine 2000 (Life Technologies, Carlsbad, Calif.) in a total of 2 mL per well of OptiMEM low serum medium (Life Technologies). For proteasome inhibition studies, MG132 was added to cells in normal medium four hours after transfection and left on overnight. 5 μM was used for western studies, and 1 μM was used for luciferase assays.

Site Directed Mutagenesis.

The cloning of TWIST1 into the pcDNA4-MycHis vector has been described previously [14]. The wild type RELA gene was also cloned into pcDNA4-MycHis, including a stop codon at the C-terminus to prevent translation of the Myc-His tag. TWIST1 retained the tag. Amino acid substitution and truncation mutations were introduced using the QuikChange II site directed mutagenesis kit (Agilent, Santa Clara, Calif.) according to the manufacturer's instructions and following their recommendations for primer design. Silent mutations were introduced in tandem with the desired mutations in order to create or eliminate restriction sites to facilitate screening for mutants. All mutations were confirmed by Sanger sequencing.

GFP Fusion Protein.

In order to create a competitive inhibitor for TWIST1-RELA binding, the WR domain from TWIST1 was fused to GFP. To achieve this, PCR was used to amplify the final 63 nucleotides of the TWIST1 gene (including stop codon) and add 5' XhoI and 3' BamHI restriction sites. The PCR fragment and the pEGFP-C3 vector were subjected to XhoI-BamHI double digest (New England BioLabs, Ipswich, Mass.) and the two were ligated together. GFP lacking the WR domain was used as a control, and includes residues at the C-terminus encoded by the multiple cloning site of the vector. As a result, the molecular weights of the two GFP proteins are indistinguishable on a western blot. To achieve equal expression of GFP-WR compared to unmodified GFP, it was necessary to transfect cells with three-fold more GFP-WR plasmid versus GFP. A one to one ratio was sufficient for CoIP illustrated in FIG. 4C. For all GFP-WR experiments, 4x refers to GFP-WR only, 3x to a 3:1 ratio of GFP-WR to GFP, 2x to equal amounts of both, 1× to a 1:3 ratio of GFP-WR to GFP, and 0 to GFP only.

Co-Immunoprecipitation.

HEK-293 cells were plated at 500,000 cells per well, in 2 mL normal medium, in a 6 well plate and allowed to adhere. The next day, medium was replaced with OptiMEM low serum medium (Life Technologies). Cells were transfected with various alleles of TWIST1, RELA, and GFP using Lipofectamine 2000 (Life Technologies). The following day, cells were lifted using trypsin, washed with PBS, and pelleted. Cell pellets were lysed in RIPA buffer, and protein concentration was determined by BCA Protein Assay (Thermo Fisher, Waltham, Mass.). 50-100 μg total protein (equal between conditions) was pre-cleared by incubating with 1 μg normal rabbit IgG (Santa Cruz Biotechnology, Dallas, Tex.) and 20-30 μL Protein A/G Agarose beads (Santa Cruz Biotechnology, sc-2003) on a rocker at 4° C. for 1 hour. Water was added to equalize volumes across conditions. Beads were spun down, and equal volumes of supernatant from each condition were transferred to new tubes, and incubated with 1 μg rabbit anti-RELA (Santa Cruz Biotechnology sc-109) or rabbit anti-GFP (Santa Cruz Biotechnology, sc-8334) antibodies on a rocker at 4° C. After 1 hour, 20-30 μL Protein A/G Agarose beads were added to each tube, and tubes were returned to the rocker at 4° C. overnight. The following day, unbound protein was removed and beads were washed five times in PBS. Beads were boiled in 20 μL 2x loading dye to release bound protein. Equal masses of input and equal volumes of immunoprecipitated protein were used for western blotting.

Cell Fractionation.

HEK-293 cells were plated and transfected as described for co-immunoprecipitation above. The following day, cells were lifted using trypsin, washed with PBS, and pelleted. Pellets were resuspended in 100 μL hypotonic buffer (10 mM HEPES, 10 mM KCl, 0.1 mM EDTA, 1 mM $Na_3VO_4$, 1.25 mM NaF, 0.4% IGEPAL, 0.5 mM DTT) in the presence of protease inhibitor (Thermo Fisher, Waltham, Mass.). Cells were left on ice 15 minutes to swell, and then lysed by addition of NP-40 to a final concentration of 0.1%. Nuclei were separated from cytoplasmic lysate by centrifugation (3000 rpm, 10 min, 4° C.) and washed once in hypotonic buffer without NP-40. Nuclei were then resuspended in 50 μL high salt buffer (20 mM HEPES, 400 mM NaCl, 1 mM EDTA, 10% glycerol, 1 mM $Na_3VO_4$, 1.25 mM NaF, 0.5 mM DTT) plus protease inhibitor. Vials were shaken for 2 hr at 250 rpm at 4° C., and then centrifuged (5 min, 14,800 rpm, 4° C.). NaCl concentration was adjusted to 137 mM by addition of water prior to western blotting.

Western Blotting.

Protein was run on 4% stacking, 10% resolving polyacrylamide gels and transferred to PVDF membrane (GE Healthcare Bio-Sciences, Pittsburgh, Pa.) on a Trans-Blot SD Semi-Dry Transfer Cell (Bio-Rad, Hercules, Calif.). Membranes were rinsed with PBS and blocked in 10% milk powder in PBS, 1 hour at room temperature or overnight at 4° C. Membranes were then incubated with mouse primary antibody in 5% milk with 0.2% Tween-20 (Ab Buffer) for 1 hour at room temperature or overnight at 4° C., followed by five 5-minute washes in PBS with 0.1% Tween-20 (PBST). Membranes were then incubated with anti-mouse secondary antibody in Ab Buffer for 1 hour at room temperature, followed by an additional five PBST washes. Primary antibodies were from Santa Cruz Biotechnology: for TWIST1, TWIST 2c1a (sc-81417) 1:250-1:500; for RELA, NF-κB p65 F-6 (sc-8008) 1:250-1:500; for GFP, GFP B-2 (sc-9996) 1:1000. Secondary antibody was WesternSure HRP Goat anti-Mouse (Li-Cor, Lincoln, Neb., 926-80010) 1:10,000. Protein was detected using FemtoGlow chemiluminescent substrate (Michigan Diagnostics, Royal Oak, Mich.) and the Pxi4 imager (Syngene, Frederick, Md.). Quantitation was performed using the accompanying GeneTools software.

Luciferase Assay.

Ovcar4 cells were plated at 50,000-75,000 cells per well, in 500 μL RPMI, in a 24 well plate and allowed to adhere overnight. The following day, cells were switched to OptiMEM medium and transfected using Lipofectamine 2000 at 2 μL per well. Plasmids were: TWIST 1 in pcDNA4, RELA in pcDNA4, Renilla luciferase, and firefly luciferase (FFluc) in pGL3. FFluc was under the control of the IL-8 promoter; construction of this vector has been described previously [14]. Empty pGL3 lacking a promoter was used as a negative control for FFluc expression. Each condition was represented by triplicate wells. The day after transfection, luciferase expression was quantified using the Dual Luciferase Assay kit (Promega, Madison, Wis.) according to the manufacturer instructions.

Data Analysis and Statistics.

Western blots were quantified using GeneTools software. Data were graphed and analyzed in Microsoft Excel and GraphPad Prism 6, respectively. All error bars show standard deviation. Luciferase assays were analyzed using one-way ANOVA with correction for multiple comparisons. For assay testing RELA mutants, all conditions were compared to all others. For assays testing TWIST1 mutants and GFP-WR inhibitor, positive control condition was compared to all others. Positive control conditions are indicated in each relevant figure. All error bars represent standard deviation. *, $p<0.05$; , $p<0.01$; *, $p<0.001$; ****, $p<0.0001$ throughout.

Results.

Single amino acid changes in the WR domain disrupt TWIST1-RELA binding.

Figure 2B:
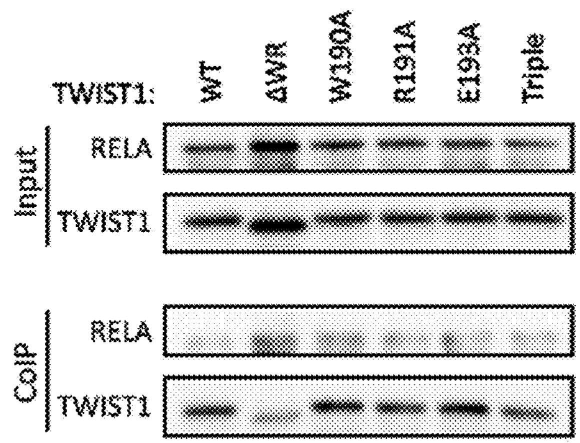
Figure 2C:
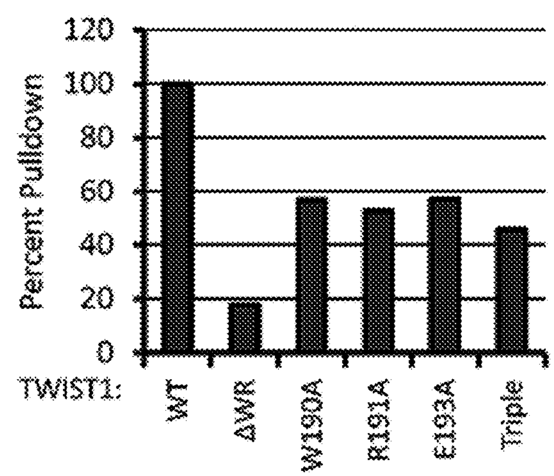

Site-directed mutagenesis was employed to generate mutations in the WR domain of TWIST1. On the basis of their high evolutionary conservation (SEQ ID NOS:1-3), we selected W190, R191, and E193 for mutation to alanine (W190A, R191A, E193A alleles, respectively). The ΔWR allele, in which all twenty amino acids of the WR domain have been deleted, was created previously as described elsewhere [14]. Mutants were screened by restriction digestion and confirmed by sequencing (data not shown). All alleles are shown schematically in FIG. 2A. In order to determine the contribution of individual amino acids in the WR domain to TWIST1-RELA binding, we transiently expressed all TWIST1 alleles in HEK293 cells and performed co-immunoprecipitation (CoIP). Following RELA pulldown, western blotting showed that as demonstrated previously, truncation of the WR domain reduced TWIST1-RELA binding to basal levels. W190A, R191A, and E193A mutations reduced TWIST1-RELA binding also, but to a lesser degree than ΔWR. A triple mutant with W190A, R191A, and E193A mutations produced a phenotype intermediate between any of the single mutants and ΔWR (FIGS. 2B-2C).

Ability of mutant TWIST1 to drive expression of IL-8 is reduced.

Figure 2D:
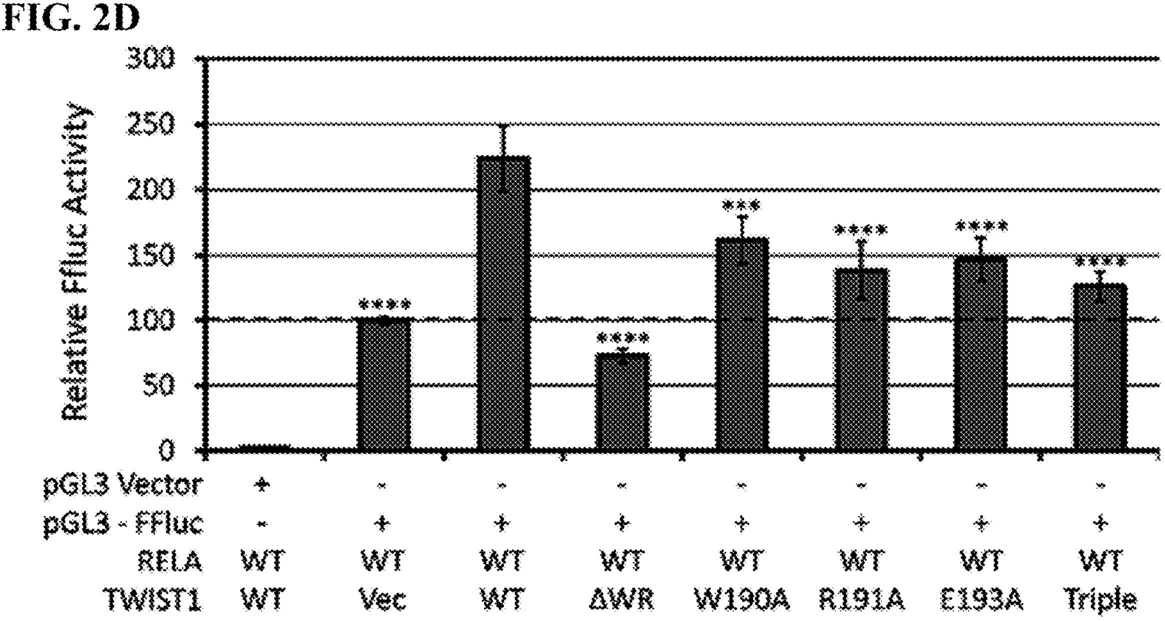

We established that TWIST1-RELA binding upregulates IL-8 expression by >2 fold over RELA alone, and that prevention of binding by truncating TWIST1 returns IL-8 expression to basal levels [14]. In order to determine the effect of W190A, R191A, and E193A mutations on IL-8 expression, we performed a dual luciferase assay in which firefly luciferase (FFluc) was under the control of the IL-8 promoter. The exogenous expression of RELA in Ovcar4 cells gave rise to a basal level of IL-8 driven FFluc, which was increased by co-expression of, and thus binding with, TWIST1 (FIG. 2D). Mirroring the phenotypes seen in our CoIP experiments above, W190A, R191A, and E193A mutations significantly reduced expression of FFluc, and the triple mutant reduced expression still further (FIG. 2D).

RELA C-terminus is required for TWIST1 binding.

Figure 3A:
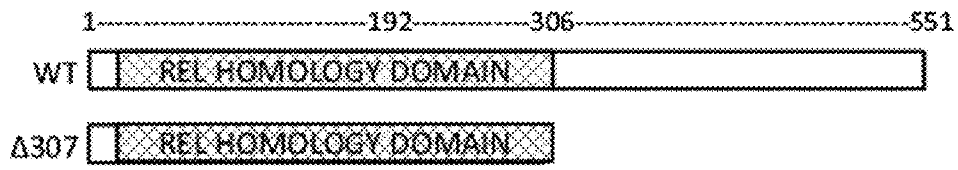
FIGS. 3A-3D. Truncation of RELA reveals TWIST1 binding domain is also required for IL-8 regulatory activity.
Figure 3B:
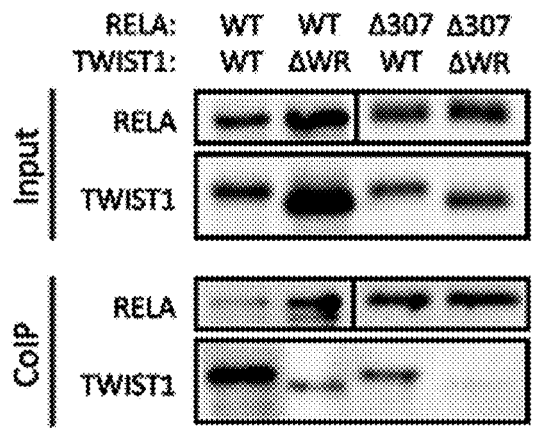
Figure 3C:
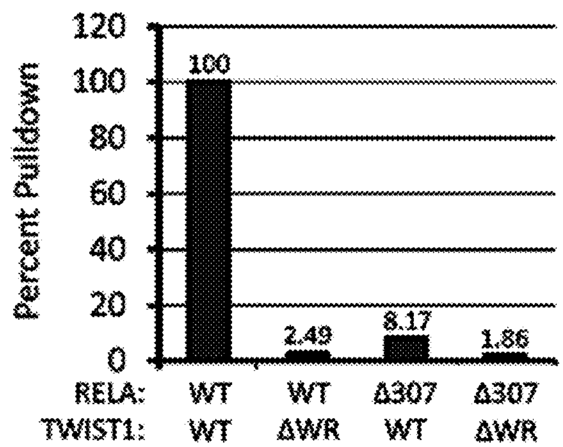

While the inventors have shown that the TWIST1 C-terminus is required for RELA binding, the binding site on RELA was as yet unknown. In order to narrow down the location of this site, the inventors created a truncation mutant of RELA, 4307 (FIG. 3A). Site directed mutagenesis was employed to insert a stop codon directly following the coding sequence for the REL homology domain, a well-conserved domain that has been structurally characterized [17]. CoIP of RELA revealed that truncation of RELA reduced TWIST1 binding to a similar degree as TWIST1 truncation (FIGS. 3B-3C). Similar results were obtained with a 4192 RELA allele, indicating that further truncation of the protein did not further reduce TWIST1 binding (data not shown). Truncating both proteins resulted in a greater inhibition of binding; under these conditions, TWIST1 was barely detectable following CoIP (FIGS. 3B-3C).

RELA C-terminus is required for IL-8 activation, independent of TWIST1 mutation status.

Figure 3D:
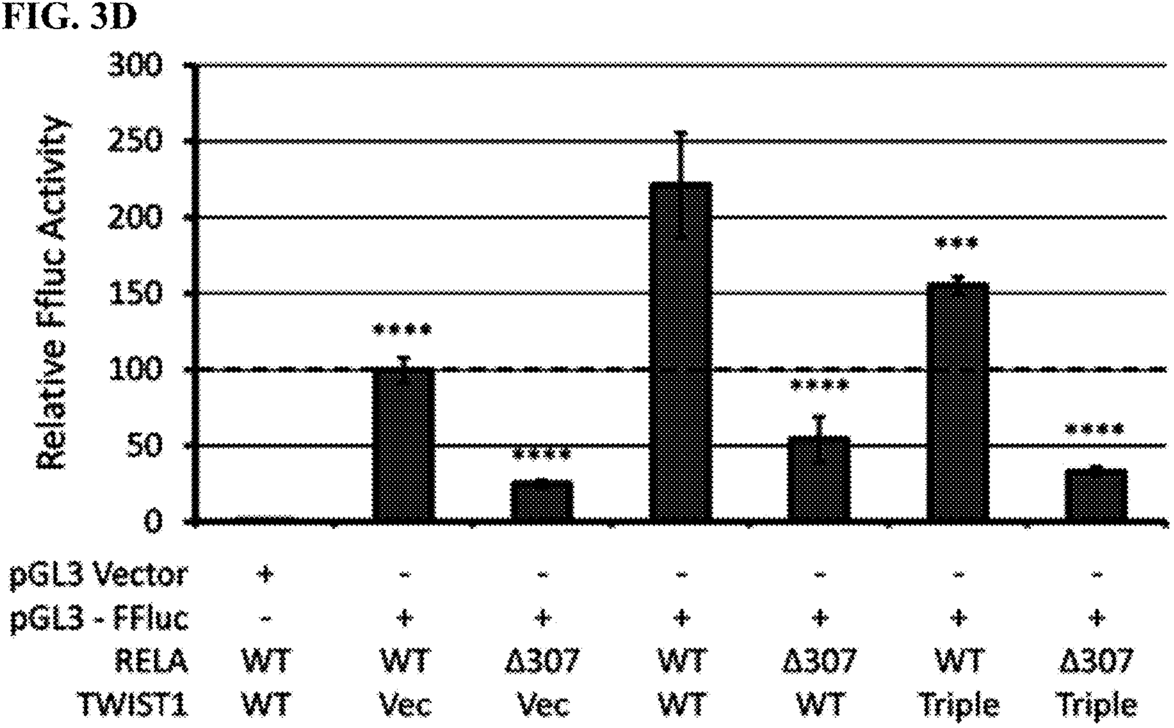

In order to verify that loss of binding between RELA 4307 and TWIST1 impacted IL-8 expression, the inventors utilized a dual luciferase assay, and the inventors demonstrated that RELA truncation was able to reduce FFluc expression (FIG. 3D). However, this phenotype was independent of TWIST1; in the absence of TWIST1, RELA 4307 showed impaired IL-8 upregulation compared to WT RELA. TWIST1 expression upregulated IL-8-driven FFluc approximately two-fold, regardless of RELA status. Co-expression of TWIST1 ΔWR with RELA led to an intermediate phenotype, for both WT and 4307 alleles of RELA (FIG. 3D). Thus, we conclude that both the transactivation and TWIST1-binding domains are contained within the relatively uncharacterized C-terminus of RELA.

Creation of a GFP-WR domain fusion protein.

Figure 4A:
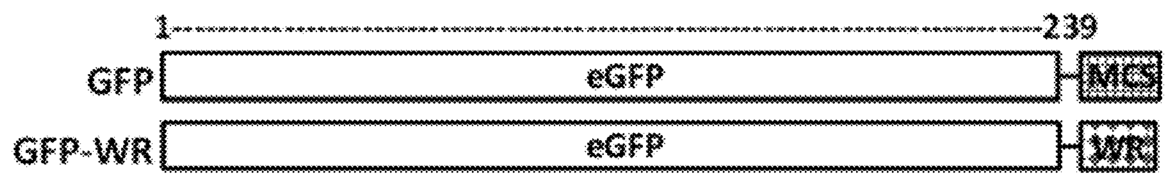
FIG. 4A-4E. Competitive inhibition of TWIST1 WR domain binding.
Figure 4B:
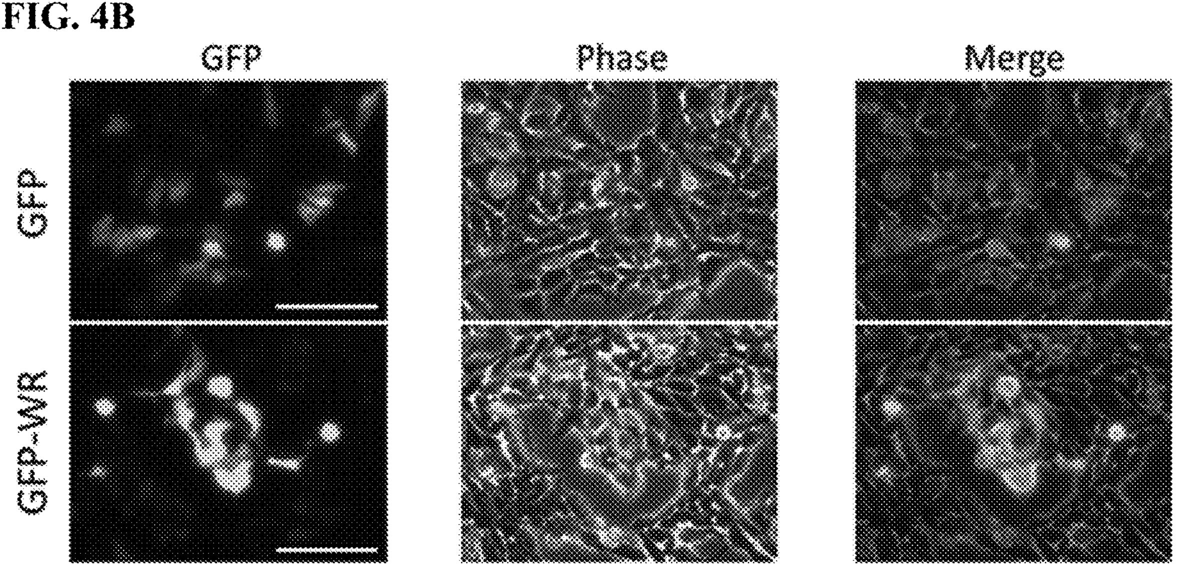

Given the demonstrated role for the WR domain in RELA binding, as well as in the transcription factor activity of TWIST1 [13,16], the inventors posit that this domain is an attractive target for therapeutic intervention. To test whether the WR domain could antagonize TWIST1-RELA binding, the WR domain was fused to GFP in the pEGFP-C3 vector (FIG. 4A). Empty pEGFP-C3 produces GFP followed by 21 residues encoded by the multiple cloning site. We therefore used this vector as a negative control, since its protein product would be of the same size as GFP-WR (FIG. 4A). Both forms of GFP were expressed to similar degrees in HEK293 cells (FIG. 4B).

GFP-WR fusion protein reduces TWIST1-RELA binding and IL-8 activation.

Figure 4C:
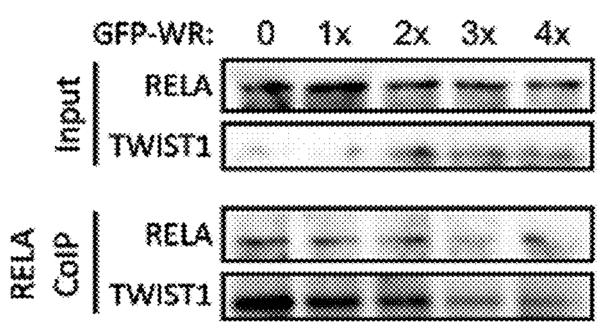
Figure 4D:
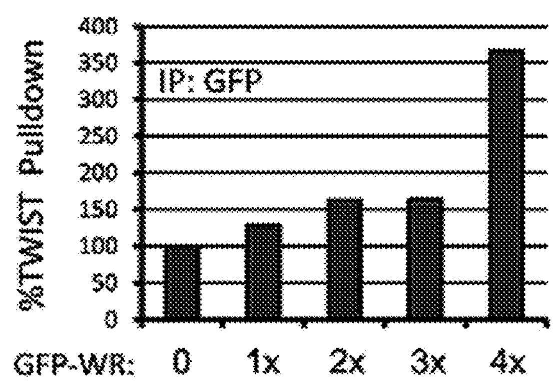
Figure 4E:
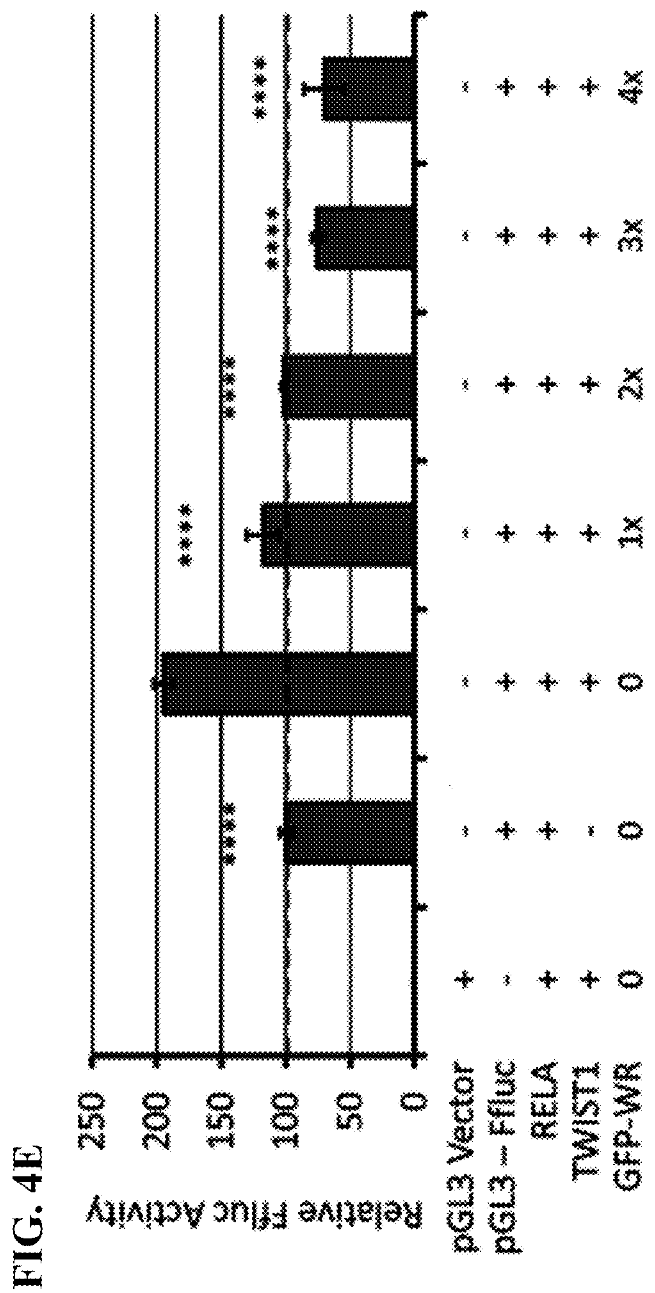

To determine the effect of GFP-WR on TWIST1-RELA binding, the inventors performed CoIP analyses. Total GFP expression in transfected cells was held constant across all conditions by supplementing GFP-WR with control GFP. RELA pulldown revealed that levels of TWIST1 co-precipitated were reduced in a dose dependent fashion with increasing GFP-WR expression (FIG. 4C). GFP pulldown revealed that only trace amounts of RELA were co-precipitated with GFP (data not shown), but that TWIST1 was co-precipitated to a greater degree with increasing GFP-WR expression (FIG. 4D). These findings indicate that GFP-WR is interacting with TWIST1 via WR-WR binding, as illustrated by recent studies of higher order TWIST1 complexes [13]. In order to determine whether GFP-WR-mediated inhibition of TWIST1-RELA binding impacted downstream signaling, the inventors employed a dual luciferase assay to quantify IL-8 promoter activity, and the inventors demonstrated that GFP-WR expression led to a dose-dependent reduction in FFluc expression (FIG. 4E). Thus, the TWIST1-driven IL-8 pathway can be inhibited by direct competition using the WR domain.

GFP-WR fusion protein sequesters TWIST1 and leads to its degradation.

Figure 5A:
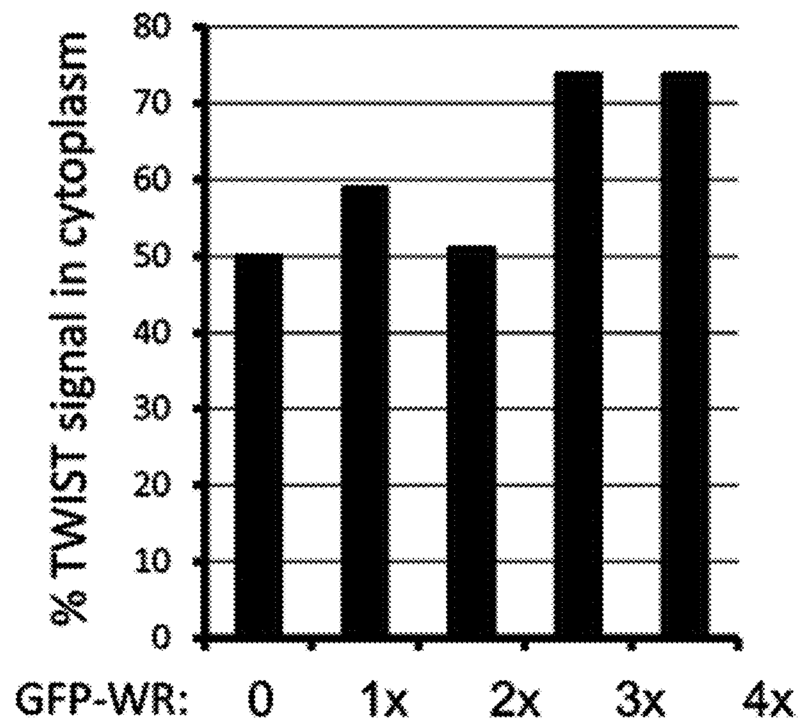
FIGS. 5A-5D. Mechanism of GFP-WR action.
Figure 5B:
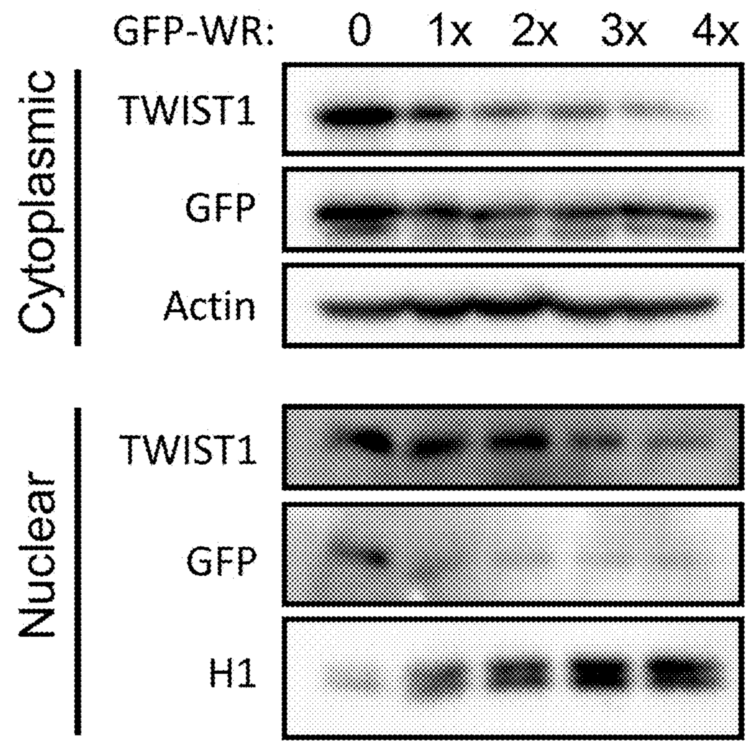
Figure 5C:
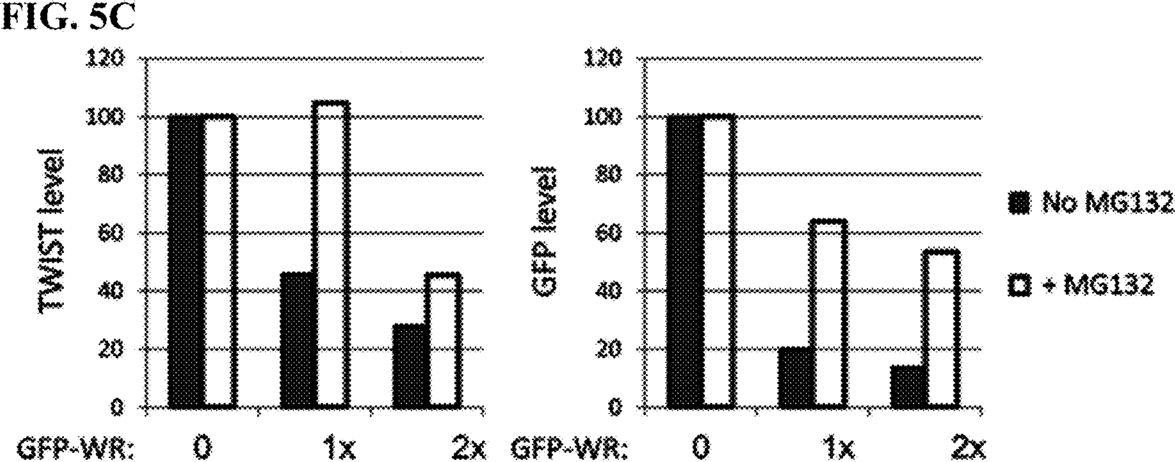
Figure 5D:
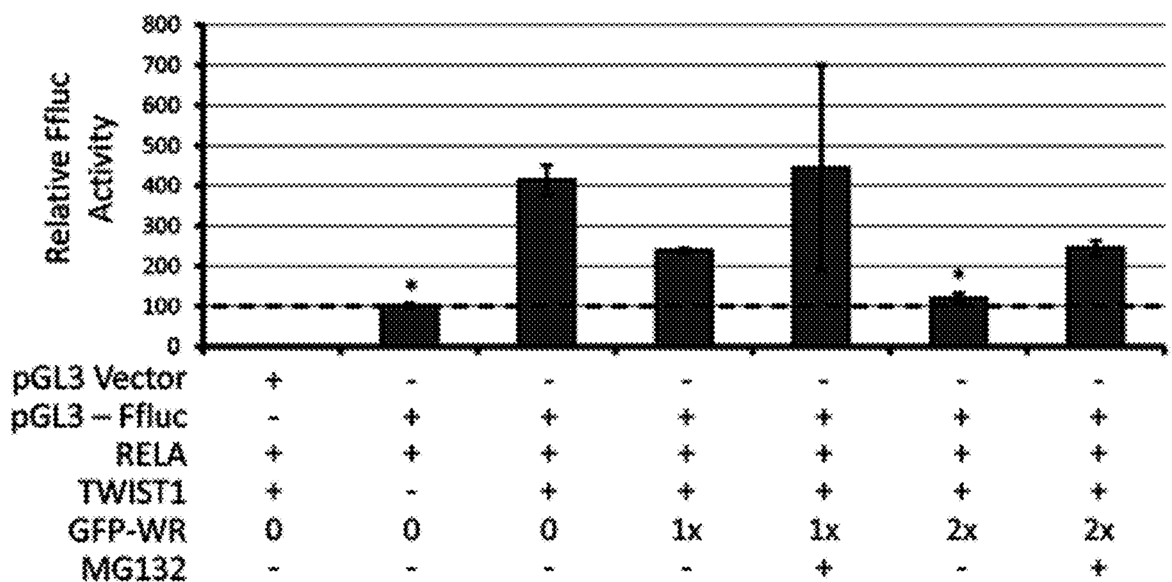

The lack of RELA binding, in concert with the mostly cytoplasmic localization of GFP-WR (FIG. 4B), implies that GFP-WR is sequestering TWIST1 in the cytoplasm. In order to confirm this hypothesis, the inventors performed cell fractionation and analyzed the levels of TWIST1 found in the cytoplasmic and nuclear fractions. Western blot of fractionated cells showed a mild increase in the proportion of TWIST1 signal found in the cytoplasmic fraction as GFP-WR transfection increased (FIG. 5A). However, in both cytoplasmic and nuclear fractions, the absolute levels of both TWIST1 and GFP present decreased as the amount of GFP-WR transfected was increased (FIG. 5B). This indicated that the interactions between these proteins may lead to their degradation, as seen for TWIST1 previously [15,18]. In order to test this hypothesis, the inventors treated cells with the proteasome inhibitor MG132 overnight. Western blots show that MG132 was able to partially rescue the levels of TWIST1 and GFP in the cytoplasmic fraction of these cells (FIG. 5C). In order to determine the effect of this rescue on IL-8 promoter activity, a dual luciferase assay was used. Treatment with MG132 resulted in partial rescue of IL-8 promoter activity, mirroring levels of TWIST following MG132 treatment (FIG. 5D).

Discussion

The inventors demonstrated that the TWIST1 WR domain was vital for TWIST1 activity, and further analyzed the specific interaction between TWIST1 and RELA. The inventors demonstrated previously that the WR domain was required for binding between these two proteins, but that TWIST1 DNA binding was dispensable [14]. The inventors further showed that the production of IL-8 was hampered by loss of binding as a result of deleting the WR domain [14].

In the present disclosure, the inventors identified three highly conserved residues within the WR domain and used alanine scanning to ascertain their role in TWIST1 activity. The inventors discovered that all three mutations led to a reduction in TWIST1-RELA binding and downstream IL-8 promoter activity; the triple mutant further reduced RELA binding and IL-8 promoter activity. These findings indicated that the central region of the WR domain (W190, R191, E193) was important for protein-protein interactions involving TWIST1. This function may explain their evolutionary sequence conservation.

No crystal structure for full length TWIST1 presently exists. However, a computational model predicts a helical structure for much of the WR domain and also suggests an interface that binds to p53 [15]. The R191 residue in particular was responsible for disrupting p53 post-translational modifications, leading to p53 degradation [15]. The inventors have shown herein that the WR domain interacts with a transactivation domain downstream of the REL homology domain, which also has yet to be structurally characterized. Other groups have shown also that the WR-domain of TWIST1 binds to Sox10 and Runx3 [19,20], and additional binding partners may still have yet to be identified. Further studies are needed to recognize structural motifs that may predict TWIST1-binding sites on additional cellular proteins.

Having shown that the bHLH domain of TWIST1 was not required for IL-8 regulation [14], the inventors hypothesized that a separation of function would be possible, and that they could independently study the DNA binding and protein binding functions of TWIST1. However, Gajula et al. showed that TWIST1 lacking the WR domain was unable to promote metastasis in an in vivo model of prostate cancer. Specifically, they found that TWIST1-mediated regulation of Hoxa9 at the transcriptional level was responsible for the phenotype they saw [16]. A possible explanation for this finding came courtesy of Chang et al, who found that TWIST1-responsive promoters contain tandem E-box sequences. Both E-boxes are bound by TWIST1 heterodimers, which then interact via their WR domains to form a transient tetramer [13]. Thus, whether directly bound to DNA or bound to protein cofactors, there is now strong evidence that WR domain interactions lie at the heart of many TWIST1 signaling processes.

Targeting of the WR domain offers a therapeutic approach to simultaneously disrupt protein transactivation, transcription factor activities, and subcellular localization of the TWIST1 protein. A GFP fusion protein including the WR domain was created and used to inhibit normal TWIST1-RELA binding and IL-8 promoter regulation. The GFP-WR fusion successfully reduced TWIST1 activity, and sequestered TWIST1 in the cytosol in a dose dependent manner. Furthermore, the inventors found that GFP-WR expression led to TWIST1 degradation. This mechanism of inhibition via sequestration and degradation has a natural analogue, supporting its efficacy: TWIST1 is known to be sequestered by HLH inhibitor of DNA binding (Id) family members 2 and 4 [21,22]. Moreover, mutations in TWIST1 found in Saethre-Chotzen Syndrome that prevent its dimerization and nuclear translocation have been shown to lead to degradation of the protein [18].

Abbreviations: EMT, epithelial to mesenchymal transition; CSC, cancer stem cell; CoIP, co-immunoprecipitation; IL-8, interleukin 8; FFluc, firefly luciferase; GFP, green fluorescent protein; GFP-WR, GFP-WR domain fusion protein; Id, inhibitor of DNA binding; FBS, fetal bovine serum; PBS, phosphate buffered saline; PBST, PBS with 0.1% Tween-20.

REFERENCES

[1] Nguyen D X, Bos P D, Massague J: Metastasis: from dissemination to organ-specific colonization. Nat Rev Cancer 2009, 9(4):274-284; [2] Trimble E L, Wright J, Christian M C: Treatment of platinum-resistant ovarian cancer. Expert opinion on pharmacotherapy 2001, 2(8): 1299-1306; [3] van Jaarsveld M T, Helleman J, Boersma A W, van Kuijk P F, van Ijcken W F, Despierre E, Vergote I, Mathijssen R H, Berns E M, Verweij J et al: miR-141 regulates KEAP1 and modulates cisplatin sensitivity in ovarian cancer cells. Oncogene 2013, 32(36):4284-4293; [4] Ferlay J, Parkin D M, Steliarova-Foucher E: Estimates of cancer incidence and mortality in Europe in 2008. Eur J Cancer 2010, 46(4):765-781; [5] Simpson P: Maternal-Zygotic Gene Interactions during Formation of the Dorsoventral Pattern in *Drosophila* Embryos. Genetics 1983, 105(3):615-632; [6] Yang J, Mani S A, Donaher J L, Ramaswamy S, Itzykson R A, Come C, Savagner P, Gitelman I, Richardson A, Weinberg R A: Twist, a master regulator of morphogenesis, plays an essential role in tumor metastasis. Cell 2004, 117(7):927-939; [7] Fu J, Qin L, He T, Qin J, Hong J, Wong J, Liao L, Xu J: The TWIST/Mi2/NuRD protein complex and its essential role in cancer metastasis. Cell Res 2011, 21(2):275-289; [8] Low-Marchelli J M, Ardi V C, Vizcarra E A, van Rooijen N, Quigley J P, Yang J: Twist1 induces CCL2 and recruits macrophages to promote angiogenesis. Cancer Res 2013, 73(2):662-671; [9] Kong D, Li Y, Wang Z, Sarkar F H: Cancer Stem Cells and Epithelial-to-Mesenchymal Transition (EMT)-Phenotypic Cells: Are They Cousins or Twins? Cancers 2011, 3(1):716-729; [10] Vesuna F, Lisok A, Kimble B, Raman V: Twist modulates breast cancer stem cells by transcriptional regulation of CD24 expression. Neoplasia (New York, N.Y.) 2009, 11(12):1318-1328; [11] Bridges R S, Kass D, Loh K, Glackin C, Borczuk A C, Greenberg S: Gene expression profiling of pulmonary fibrosis identifies Twist1 as an antiapoptotic molecular "rectifier" of growth factor signaling. The American journal of pathology 2009, 175(6):2351-2361; [12] Murray S S, Glackin C A, Winters K A, Gazit D, Kahn A J, Murray E J: Expression of helix-loop-helix regulatory genes during differentiation of mouse osteoblastic cells. Journal of bone and mineral research: the official journal of the American Society for Bone and Mineral Research 1992, 7(10):1131-1138; [13] Chang A T, Liu Y, Ayyanathan K, Benner C, Jiang Y, Prokop J W, Paz H, Wang D, Li H R, Fu X D et al: An evolutionarily conserved DNA architecture determines target specificity of the TWIST family bHLH transcription factors. Genes Dev 2015, 29(6):603-616; [14] Li S, Kendall S E, Raices R, Finlay J, Covarrubias M, Liu Z, Lowe G, Lin Y H, Teh Y H, Leigh V et al: TWIST1 associates with NF-kappaB subunit RELA via carboxyl-terminal WR domain to promote cell autonomous invasion through IL8 production. BMC Biol 2012, 10:73; [15] Piccinin S, Tonin E, Sessa S, Demontis S, Rossi S, Pecciarini L, Zanatta L, Pivetta F, Grizzo A, Sonego M et al: A “twist box” code of p53 inactivation: twist box: p53 interaction promotes p53 degradation. Cancer Cell 2012, 22(3):404-415; [16] Gajula R P, Chettiar S T, Williams R D, Thiyagarajan S, Kato Y, Aziz K, Wang R, Gandhi N, Wild A T, Vesuna F et al: The twist box domain is required for Twist1-induced prostate cancer metastasis. Molecular cancer research: MCR 2013, 11(11):1387-1400; [17] Chen Y Q, Ghosh S, Ghosh G: A novel DNA recognition mode by the NF-kappa B p65 homodimer. Nat Struct Biol 1998, 5(1):67-73; [18] El Ghouzzi V, Legeai-Mallet L, Aresta S, Benoist C, Munnich A, de Gunzburg J, Bonaventure J: Saethre-Chotzen mutations cause TWIST protein degradation or impaired nuclear location. Hum Mol Genet 2000, 9(5): 813-819; [19] Vincentz J W, Firulli B A, Lin A, Spicer D B, Howard M J, Firulli A B: Twist1 controls a cell-specification switch governing cell fate decisions within the cardiac neural crest. PLoS Genet 2013, 9(3): e1003405; [20] Pham D V J, Firulli A B, Kaplan M H: Twist1 regulates Ifng expression in Thl cells by interfering with Runx3 function. J Immunol 2012, 189(2):832-840; [21] Yang J, Velikoff M, Agarwal M, Disayabutr S, Wolters P J, Kim K K: Overexpression of inhibitor of DNA-binding 2 attenuates pulmonary fibrosis through regulation of c-Abl and Twist. The American journal of pathology 2015, 185(4):1001-1011; [22] Rahme G J, Israel M A: Id4 suppresses MMP2-mediated invasion of glioblastoma-derived cells by direct inactivation of Twist1 function. Oncogene 2015, 34(1):53-62; [23] Finlay J, Roberts C M, Lowe G, Loeza J, Rossi J J, Glackin C A: RNA-based TWIST1 inhibition via dendrimer complex to reduce breast cancer cell metastasis. BioMed research international 2015, 2015:382745; [24] Finlay J, Roberts C M, Dong J, Zink J I, Tamanoi F, Glackin C A: Mesoporous silica nanoparticle delivery of chemically modified siRNA against TWIST1 leads to reduced tumor burden. Nanomedicine: nanotechnology, biology, and medicine 2015, 11(7):1657-1666; [25] Wang S M C V, Pignolo R J, Rotenberg M O, Cristofalo V J, Sierra F: Cloning of the human twist gene: its expression is retained in adult mesodermally-derived tissues. Gene 1997, 187(1):83-92; [26] Haslehurst A M, Koti M, Dharsee M, Nuin P, Evans K, Geraci J, Childs T, Chen J, Li J, Weberpals J et al: EMT transcription factors snail and slug directly contribute to cisplatin resistance in ovarian cancer. BMC Cancer 2012, 12:91; [27] Wang Y, Qu Y, Niu X L, Sun W J, Zhang X L, Li L Z: Autocrine production of interleukin-8 confers cisplatin and paclitaxel resistance in ovarian cancer cells. Cytokine 2011, 56(2):365-375;

What is claimed is:

1. A composition comprising a TWIST peptide or a nucleic acid encoding said TWIST peptide covalently bound to a delivery vehicle, wherein said TWIST peptide comprises a WR domain of TWIST1.

2. A fusion protein comprising a TWIST peptide covalently attached to a cell-penetrating peptide, wherein said TWIST peptide comprises a WR domain of TWIST1.

3. A nucleic acid sequence encoding said fusion protein of claim 2.

4. The nucleic acid sequence of claim 3, wherein said nucleic acid sequence is part of a vector sequence.

5. The composition of claim 1, wherein the TWIST peptide comprises an amino acid sequence comprising at least 80% sequence identity to SEQ ID NO: 1.

6. The composition of claim 5, wherein the TWIST peptide comprises an amino acid sequence of SEQ ID NO: 1.

7. The composition of claim 1, wherein the delivery vehicle is a nanoparticle, a vector, a virus capsid, a liposome, a liposomal vesicle, a lipoplex, a polyplex, a dendrimer, a macrophage, a polymer, a hybrid particle, or a lipid vehicle.

8. The fusion protein of claim 2, wherein the cell-penetrating peptide comprises an amino acid sequence of SEQ ID NO:4.

9. The fusion protein of claim 2, wherein the cell penetrating peptide comprises an amino acid sequence of SEQ ID NO:5, SEQ ID NO:16, SEQ ID NO:17, SEQ ID NO:18, SEQ ID NO:19, SEQ ID NO:20, SEQ ID NO:21, SEQ ID NO:22, SEQ ID NO:23.

10. The fusion protein of claim 2, wherein the cell penetrating peptide comprises an amino acid sequence of SEQ ID NO:6, SEQ ID NO:7, SEQ ID NO:8, SEQ ID NO:9, SEQ ID NO:10, or SEQ ID NO:11.

11. The composition of claim 1, further comprising an anti-cancer agent.

12. The composition of claim 11, wherein the anti-cancer agent is doxorubicin, cisplatin, carboplatin, a taxane, camptothecin, or a combination of two or more thereof.

13. The composition of claim 1, further comprising a pharmaceutically acceptable excipient.

14. The nucleic acid sequence of claim 4, wherein the vector sequence is a plasmid vector sequence or a viral vector sequence.

15. A composition comprising a TWIST peptide or a nucleic acid encoding said TWIST peptide bound to a delivery vehicle, wherein said TWIST peptide comprises a WR domain of TWIST1, and wherein said delivery vehicle is a nanoparticle, a vector, a virus capsid, a liposome, a liposomal vesicle, a lipoplex, a polyplex, a dendrimer, a macrophage, a polymer, a hybrid particle, or a lipid vehicle.

16. The composition of claim 15, wherein said TWIST peptide comprises an amino acid sequence comprising at least 80% sequence identity to SEQ ID NO: 1.

17. The composition of claim 16, wherein said TWIST peptide comprises an amino acid sequence of SEQ ID NO: 1.

18. The composition of claim 15, further comprising an anti-cancer agent.

19. The composition of claim 18, wherein the anti-cancer agent is doxorubicin, cisplatin, carboplatin, a taxane, camptothecin, or a combination of two or more thereof.

20. The composition of claim 15, further comprising a pharmaceutically acceptable excipient.

* * * * *

UNITED STATES PATENT AND TRADEMARK OFFICE

CERTIFICATE OF CORRECTION

PATENT NO. : 10,946,061 B2
APPLICATION NO. : 16/843718
DATED : March 16, 2021
INVENTOR(S) : Carlotta A. Glackin It is certified that error appears in the above-identified patent and that said Letters Patent is hereby corrected as shown below:

In the Specification

At Column 1, Lines 16 to 19, delete "This invention was made with Government support under grant number P30 CA33572 awarded by the National Institutes of Health. The Government has certain rights in the invention." and insert --This invention was made with government support under P30 CA033572 awarded by the National Institutes of Health. The government has certain rights in the invention.--

Signed and Sealed this
Seventh Day of October, 2025

John A. Squires
*Director of the United States Patent and Trademark Office*